United States Patent [19]

Suzuki et al.

[11] Patent Number: 4,994,468
[45] Date of Patent: Feb. 19, 1991

[54] IMIDAZOQUINOLONE DERIVATIVES

[75] Inventors: Fumio Suzuki, Mishima; Takeshi Kuroda; Yoshisuke Nakazato, both of Shizuoka; Kenji Ohmori, Mishima; Haruhiko Manabe, Shizuoka, all of Japan

[73] Assignee: Kyowa Hakko Kogyo Co., Ltd., Tokyo, Japan

[21] Appl. No.: 489,025

[22] Filed: Mar. 5, 1990

[30] Foreign Application Priority Data

Mar. 7, 1989 [JP] Japan .................. 1-54148

[51] Int. Cl.$^5$ .................. A61K 31/47; C07D 471/04
[52] U.S. Cl. .................. 514/293; 546/82
[58] Field of Search .................. 546/82; 514/293

[56] References Cited

U.S. PATENT DOCUMENTS 4,689,338 8/1987 Gerster .................. 514/293
4,698,348 10/1987 Gerster .................. 514/293

Primary Examiner—Mary C. Lee
Assistant Examiner—Joseph K. McKane
Attorney, Agent, or Firm—Fitzpatrick, Cella, Harper & Scinto

[57] ABSTRACT

Novel imidazoquinolone derivative represented by the formula (I);

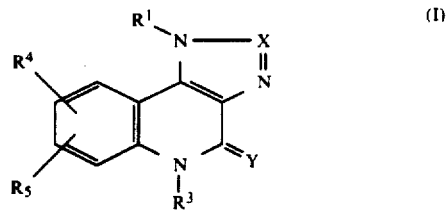

wherein $R^1$ represents hydrogen, alkyl, cycloalkyl, alkenyl aralkyl, aralkenyl or substituted or unsubstituted aryl; X represents nitrogen or

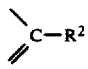

where $R^2$ is hydrogen, hydroxyl, alkyl, cycloalkyl, alkenyl, aralkyl, aralkenyl, substituted or unsubstituted aryl, thiol, halogen, substituted or unsubstituted aromatic heterocyclic group, or $-(CH_2)_mCO_2R^6$ where $R^6$ is hydrogen or lower alkyl and m is an integer of 0 to 3; Y represents oxygen or sulfur; $R^3$ represents alkyl, cycloalkyl, alkoxyalkly, alkenyl, aralkyl, aralkenyl, $-(CH_2)_n-$ Het where Het is substituted or unsubstituted aromatic heterocyclic group and n is an integer of 1 to 3 or $-(CH_2)_nCO_2R^{6a}$ where n has the same meaning as defined above and $R^{6a}$ has the same meaning as defined as to $R^6$; each of $R^4$ and $R^5$ independently represents hydrogen, lower alkyl, trifluoromethyl, cycloalkyl, halogen, hydroxyl, lower alkoxyl, lower alkylthio, nitro, amino, lower alkylamino, lower alkanoylamino, aroylamino, lower alkanoyl or aroyl; and a pharmaceutically acceptable salt thereof. The Compound (I) and a pharmaceutically acceptable salt thereof show bronchodilatory and antiallergic activities, and are useful for treating respiratory disorders such as bronchial asthma.

8 Claims, No Drawings

IMIDAZOQUINOLONE DERIVATIVES

BACKGROUND OF THE INVENTION

The present invention relates to novel imidazoquinolone derivatives having a 1H, 5H-imidazo[4,5-c]quinolin-4-one skeleton and showing broncho-dilatory and antiallergic activities.

1H-imidazo[4,5-c]quinolines useful as a broncho-dilator and 1H-imidazo[4,5-c]quinoline-4-amines useful as an antiviral agent, represented by the following formula are disclosed in Japanese Published Unexamined Patent Application No. 123488/85 [U.S. Pat. Nos. 4698348 and 4689338, and EP-A-145340]

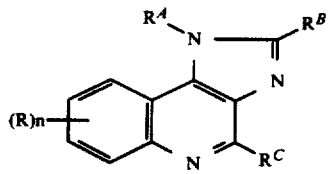

wherein $R^A$ represents hydrogen, alkyl, benzyl, phenyl, etc.; $R^B$ represents hydrogen, alkyl, etc.; and $R^c$ represents hydrogen, hydroxyl, alkylamino, etc.

SUMMARY OF THE INVENTION

An object of the present invention is to provide a novel imidazoquinolone derivative, based on a finding that compounds having a substituent at the 5-position of 1H,5H-imidazo[4,5-c]quinolin-4-ones show distinguished broncho-dilatory and/or antiallergic effect. The compounds are useful for treating respiratory disorders such as bronchial asthma.

In accordance with the present invention, there is provided an imidazoquinolone derivative represented by the formula (I);

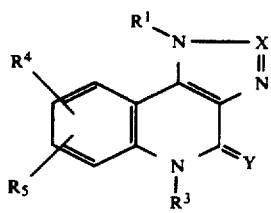

wherein $R^1$ represents hydrogen, alkyl, cycloalkyl, alkenyl, aralkyl, aralkenyl, or substituted or unsubstituted aryl; X represents nitrogen or

where $R^2$ is hydrogen, hydroxyl, alkyl, cycloalkyl, alkenyl, aralkyl, aralkenyl, substituted or unsubstituted aryl, thiol, halogen, or substituted or unsubstituted aromatic heterocyclic group, or $-(CH_2)_mCO_2R^6$ where $R^6$ is hydrogen or lower alkyl and m is an integer of 0 to 3; Y represents oxygen or sulfur; $R^3$ represents alkyl, cycloalkyl, alkoxyalkyl, alkenyl, aralkyl, aralkenyl, $-(CH_2)_n-$Het where Het is substituted or unsubstituted aromatic heterocyclic group and n is an integer of 1 to 3, or $-(CH_2)_nCO_2R^{6a}$ where n has the same meaning as defined above $R^{6a}$ has the same meaning as defined as to $R^6$; each of $R^4$ and $R^5$ independently represents hydrogen, lower alkyl, trifluoromethyl, cycloalkyl, halogen, hydroxyl, lower alkoxyl, lower alkylthio, nitro, amino, lower alkylamino, lower alkanoylamino, aroylamino, lower alkanoyl or aroyl; or a pharmaceutically acceptable salt thereof.

DETAILED DESCRIPTION OF THE INVENTION

In the definition of the respective groups in the formula (I), the alkyl or the alkyl moiety of the alkoxyalkyl means alkyls having 1 to 10 carbon atoms and includes, for example, methyl, ethyl, n-propyl, isopropyl, n-butyl, isobutyl, sec-butyl, tert-butyl, n-pentyl, neopentyl, n-hexyl, heptyl, octyl, nonyl, decyl, etc. The cycloalkyl includes alicyclic hydrocarbon groups having 3 to 8 carbon atoms such as cyclopropyl, cyclopentyl, cyclohexyl, cyclooctyl, etc. The alkenyl includes alkenyls having 2 to 6 carbon atoms such as vinyl, allyl, propenyl, isopropenyl, butenyl, hexenyl, etc. The aralkyl includes aralkyls having 7 to 15 carbon atoms such as benzyl, phenetyl, benzhydryl, etc. The aralkenyl includes aralkenyls having 8 to 18 carbon atoms, such as styryl, cinnamyl, etc. The aryl includes aryls having 6 to 10 carbon atoms such as phenyl, naphthyl, etc. The substituent in the substituted aryl includes one or two of the same or different lower alkyl, trifluoromethyl, hydroxyl, lower alkoxyl, lower alkylthio, nitro, halogen, amino, lower alkylamino, lower alkanoylamino, lower alkoxycarbonyl, lower alkanoyl, aroyl, etc. The aromatic heterocyclic group includes heterocyclic rings of 5 or 6 members such as thienyl, furyl, pyrazolyl, oxazolyl, imidazolyl, pyridyl, etc. and the substituent in the substituted aromatic heterocyclic group includes one or two of the same or different lower alkyl, lower alkoxyl, halogen, etc. The lower alkyl and the alkyl moiety of the lower alkoxyl, lower alkylthio, lower alkylamino and lower alkoxycarbonyl mean a straight or branched alkyl having 1 to 6 carbon atoms and include, for example, methyl, ethyl, n-propyl, isopropyl, n-butyl, isobutyl, sec-butyl, tert-butyl, n-pentyl, neopentyl, n-hexyl, etc. The lower alkanoyl and the alkanoyl moiety of the lower alkanoylamino include alkanoyl having 1 to 6 carbon atoms such as formyl, acetyl, propionyl, butyryl, isobutyryl, pivaloyl, valeryl, isovaleryl, etc. The aroyl and the aroyl moiety of the aroylamino include, for example, benzoyl, toluyl, propylbenzoyl, naphthoyl, etc. The halogen means fluorine, chlorine, bromine and iodine.

The pharmaceutically acceptable salt of Compound (I) includes pharmaceutically acceptable acid addition salts, metal salts, ammonium salts, organic amine addition salts, amino acid addition salts, etc.

The pharmaceutically acceptable acid addition salts of Compound (I) include inorganic acid salts such as hydrochlorides, sulfates, phosphates, etc., and organic acid salts such as acetates, maleates, fumarates, tartrates, citrates, etc. The pharmaceutically acceptable metal salts include alkali metal salts such as sodium salts, potassium salts, etc., alkaline earth metal salts such as magnesium salts, calcium salts, etc., and aluminium salts and zinc salts. The pharmaceutically acceptable organic amine addition salts include addition salts of morpholine, piperidine, etc. The pharmaceutically acceptable amino acid addition salts include addition salts of lysine, glycine, phenylalanine, etc.

Processes for preparing Compounds (I) are set forth below.

When the defined groups are changed under the conditions of the following processes or are inadequate to proceeding of the following processes, processes can be readily carried out by a usual method in the organic synthetic chemistry, for example, by protection of functional groups, elimination of protecting groups.

Process 1

A Compound (Ia) which is Compound (I) wherein X is

is obtained by reacting a Compound (II) represented by the following formula;

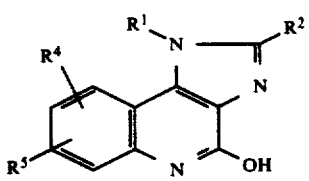

wherein $R^1$, $R^2$, $R^4$ and $R^5$ have the same meanings as defined above, with a Compound (III) represented by the following formula;

$R^3$—Z     (III)

wherein $R^3$ has the same meaning as defined above and Z is a leaving group, preferably in the presence of a base.

The leaving group represented by Z includes, for example, halogen such as chlorine, bromine, iodine, etc., alkylsulfonyloxy such as methanesulfonyloxy, etc., and arylsulfonyloxy such as phenylsulfonyloxy, p-toluenesulfonyloxy, etc.

The starting Compound (II) is synthesized by a known method as described in Japanese Published Unexamined Patent Application No. 123488/85 [U.S. Pat. Nos. 4698348 and 4689338, and EP-A-145340] or a similar method.

The base for use in the process includes alkali metal carbonates such as potassium carbonate, sodium carbonate, etc., alkali metal hydrides such as sodium hydride, etc. and alkali metal alkoxides such as sodium methoxide, sodium ethoxide, etc.

The reaction solvent for use in the process is uneffective in reaction and includes, for example, ethers such as tetrahydrofuran, dioxane, etc. amides such as dimethylformamide, etc., alcohols such as methanol, ethanol, etc., dimethylsulfoxide, which is used alone or in combination.

The reaction proceeds at a temperature of 0° to 180° C. for 30 minutes to 24 hours.

Process 2

A compound (Iaa), which is Compound (Ia) wherein $R^2$ is a group other than halogen, hydroxyl or thiol is also obtained from the following steps of reaction.

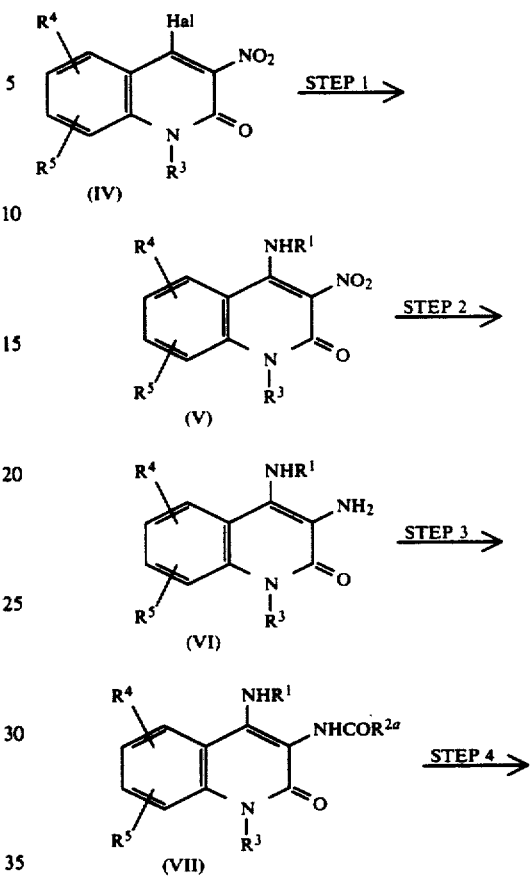

wherein $R^{2a}$ has the same meaning as defined as to $R^2$, excluding halogen, hydroxyl or thiol; Hal represents halogen and $R^1$, $R^2$, $R^3$, $R^4$ and $R^5$ have the same meanings as defined above.

The halogen represented by Hal includes chloride, bromine, iodine, etc.

The starting Compound (IV) is synthesized by a known method as described in J. Heterocyclic Chem., 18, 917 (1981) or by a similar method.

Step 1

Compound (V) is obtained by reacting Compound (IV) with an amine (VIII) represented by the following formula:

$R^1NH_2$     (VIII)

wherein $R^1$ has the same meaning as defined above, if necessary in the presence of a base.

The same reaction solvent, base, etc. as used in Process 1 are likewise used.

Step 2

Compound (VI) is obtained by catalytic reduction of Compound (V) in the presence of a catalyst of palladium/carbon or platinum oxide.

Step 3

Compound (VII) is obtained by reacting Compound (VI) with carboxylic acid (IX) represented by the following formula:

$$R^{2a}COOH \qquad (IX)$$

wherein $R^{2a}$ has the same meaning as defined above, or its reactive derivative at a temperature of $-10°$ to $50°$ C.

Preferably, the reaction with Compound (IX) is performed in the presence of a condensing agent such as thionyl chloride, N,N'-dicyclohexylcarbodiimide (DCC), polyphosphoric acid, etc., and the reactive derivative includes, for example, acid halides such as acid chlorides, acid bromides, etc., acid anhydrides, mixed acid anhydrides such as ethyl chlorocarbonate, isobutyl chlorocarbonate, etc., active esters such as p-nitrophenyl ester, N-hydroxysuccinimide ester, etc., and ortho esters.

step 4

Compound (Iaa) is obtained by heating Compound (VII) in a reaction solvent at 50° to 250° C., preferably 100° to 250° C., if necessary, in the presence of ring-closing agent.

The ring-closing agent includes polyphosphoric acid, polyphosphoric acid ester, sulfuric acid, acetic acid, phosphorus pentoxide, phosphorus pentachloride, phosphorus oxychloride, phosphorus trichloride, phosphorus tribromide, thionyl chloride, etc.

The reaction solvent includes hexamethylphosphoramide, diphenyl ether, glycerintriethyl ether, butyl ether, isoamyl ether, diethyleneglycol, triethyleneglycol, Dowtherm A (made by Dow Chemical Group, USA), etc.

Process 3

A compound (Ib), which is Compound (I) wherein $R^4$ and/or $R^5$ are groups other than hydrogen is obtained by functionalizing, for example, nitrating, halogenizing, alkanoylizing, aroylizing, etc., a Compound (Ic), which is Compound (I) wherein the corresponding group on the benzen ring is hydrogen.

For example, the nitration reaction proceeds with a nitrating agent such as nitric acid, fuming nitric acid, potassium nitrate, etc. in a solvent or free of a solvent, preferably in the presence of sulfuric acid, acetic anhydride, etc. in a solvent at a reaction temperature of $-50°$ to 100° C. As the solvent, those taking no part in the reaction such as organic acid, for example, acetic acid, etc., halogenated hydrocarbons, for example, methylene chloride, chloroform etc. are used.

The halogenation reaction proceeds with a halogen for example, chlorine, bromine, iodine etc., a halogenating agent, such as copper halide, N-halosuccinimide, etc., preferably in the presence of iron, iodide or peroxides such as perbenzoic acid, etc. or under irradiation of light at a reaction temperature of $-50°$ to 150° C.

The alkanoylization reaction and aroylization reaction proceed under the condition of Friedel-Craft type reaction using an acylating agent such as an acid halide, an acid anhydride, and active ester, etc. of the corresponding carboxylic acid and a Lewis acid catalyst such as aluminium halide, etc. in a solvent at a reaction temperature of $-50°$ to 150° C. As the solvent, those taking no part in the reaction such as halogenated hydrocarbon for example, methylene chloride, chloroform etc., carbon disulfide, etc. are used.

Process 4

Compound (Iab), which is Compound (Ia) wherein $R^2$ is hydroxyl or thiol is obtained from Compound (VI) used in process 2 as a starting compound.

Compounds (Iab'), which is Compound (Iab) wherein $R^2$ is hydroxyl, is obtained by reacting Compound (VI) with for example, phosgen, carbonyldiimidazol, urea etc. in a solvent at a reaction temperature of 0° to 150° C. As the solvent, those taking no part in the reaction such as alcohols, for example, methanol, ethanol, etc., ethers for example, tetrahydrofuran dioxane, etc., halogenated hydrocarbons, for example, chloroform, etc. are used.

Compounds (Iab") which is Compound (Iab) wherein $R^2$ is thiol is obtained by reacting Compound (VI) with thiophosgen, thiocarbonyldiimidazole, thiourea, etc. in the same manner as in the case of Compound (Iab's) wherein $R^2$ is hydroxyl.

Process 5

Compound (Id), which is Compound (I) wherein X is nitrogen, is obtained by reacting Compound (VI), used in process 2, as a starting Compound with, for example, sodium nitrite, in a solvent of alcohol-acid system at a reaction temperature of 0° to 150° C. The alcohol as the solvent includes methanol and ethanol, and the acid, as the solvent includes hydrochloric acid, acetic acid, phosphoric acid, etc.

In these processes, intermediates and desired compounds are isolated and purified by purification methods conventionally used in the organic synthetic chemistry, for example, filtration, extraction, washing, drying, concentration, recrystallization, various column chromatographies, etc.. The intermediates can be immediately used in the subsequent reaction, without any particular purification.

In case where salts of Compound (I) are desired to be obtained, (1) when Compounds (I) are obtained in the form of a salt, compounds (I) are purified as such; (2) when the compounds (I) are obtained in a free form, salts are formed in a conventional manner.

Compounds (I) and their pharmaceutically acceptable salts may exist in the form of additional products to water or various solvents, and these additional products are included in the present invention.

Preferred Compounds of the present invention are shown in Table 1. Compound Nos. (1), (2), . . . are hereinafter referred to as Compounds 1, 2, . . .

TABLE 1

| Compound No. | Name of Compound |
|---|---|
| (1) | 5-n-Butyl-1-methyl-1H,5H-imidazo[4,5-c]quinolin-4-one |
| (2) | 5-tert-Butoxycarbonylmethyl-1-methyl-1H,5H-imidazo[4,5-c]quinolin-4-one |
| (3) | 5-Furfuryl-1-methyl-1H,5H-imidazo[4,5-c]quinolin-4-one |
| (4) | 1,5-Dimethyl-1H,5H-imidazo[4,5-c]quinolin-4-one |
| (5) | 5-Ethyl-1-methyl-1H,5H-imidazo[4,5-c]quinolin-4-one |
| (6) | 1-Methyl-5-n-propyl-1H,5H-imidazo[4,5-c]quinolin- |

TABLE 1-continued

| Compound No. | Name of Compound |
|---|---|
| (7) | 1-Benzyl-5-n-butyl-1H,5H-imidazo[4,5-c]quinolin-4-one |
| (8) | 5-n-Butyl-1H,5H-imidazo[4,5-c]quinolin-4-one |
| (9) | 5-Carboxymethyl-1-methyl-1H,5H-imidazo[4,5-c]quinolin-4-one |
| (10W) | 5-n-Butyl-1-methyl-2-phenyl-1H,5H-imidazo[4,5-c]quinolin-4-one hydrochloride |
| (11W) | 5-n-Butyl-1,2-dimethyl-1H,5H-imidazo[4,5-c]quinolin-4-one hydrochloride |
| (12) | 2,8-Dibromo-5-n-butyl-1-methyl-1H,5H-imidazo[4,5-c]quinolin-4-one |
| (13) | 8-Bromo-5-n-butyl-1-methyl-1H,5H-imidazo[4,5-c]quinolin-4-one |
| (14) | 5-n-Butyl-1-methyl-8-nitro-1H,5H-imidazo[4,5-c]quinolin-4-one |
| (15W) | 5-n-Butyl-2-furyl-1-methyl-1H,5H-imidazo[4,5-c]quinolin-4-one hydrochloride |
| (16W) | 5-n-Butyl-1-ethyl-1H,5H-imidazo[4,5-c]quinolin-4-one hydrochloride |
| (17W) | 5-n-Butyl-1-n-propyl-1H,5H-imidazo[4,5-c]quinolin-4-one hydrochloride |
| (18W) | 5-n-Butyl-1-isopropyl-1H,5H-imidazo[4,5-c]quinolin-4-one hydrochloride |
| (19W) | 1,5-Di-n-butyl-1H,5H-imidazo[4,5-c]quinolin-4-one hydrochloride |
| (20W) | 5-n-Butyl-2-(4-methoxyphenyl)-1-methyl-1H,5H-imidazo[4,5-c]quinolin-4-one hydrochloride |
| (21W) | 5-n-Butyl-2-(3,4-dichlorophenyl)-1-methyl-1H,5H-imidazo[4,5-c]quinolin-4-one hydrochloride |
| (22W) | 5-n-Butyl-2-cyclopentyl-1-methyl-1H,5H-imidazo[4,5-c]quinolin-4-one hydrochloride |
| (23W) | 5-n-Butyl-7,8-dimethoxy-1-methyl-1H,5H-imidazo[4,5-c]quinolin-4-one hydrochloride |
| (24W) | 5-n-Butyl-7-chloro-1-methyl-1H,5H-imidazo[4,5-c]quinolin-4-one hydrochloride |
| (25) | 5-n-Butyl-8-chloro-1-methyl-1H,5H-imidazo[4,5-c]quinolin-4-one |
| (26) | 5-n-Butyl-1,8-dimethyl-1H,5H-imidazo[4,5-c]quinolin-4-one |
| (27W) | 5-n-Butyl-1,9-dimethyl-1H,5H-imidazo[4,5-c]quinolin-4-one hydrochloride |
| (28W) | 5-n-Butyl-1-methyl-1H,5H-imidazo[4,5-c]quinoline-4-thione hydrochloride |
| (29) | 1-Phenyl-5-n-butyl-1H,5H-imidazo[4,5-c]quinolin-4-one |
| (30) | 5-n-Butyl-2-hydroxy-1-methyl-1H,5H-imidazo[4,5-c]quinolin-4-one |
| (31) | 5-n-Butyl-1-methyl-2-mercapto-1H,5H-imidazo[4,5-c]quinolin-4-one |
| (32) | 5-n-Butyl-1-methyl-1H,5H-triazolo[4,5-c]quinolin-4-one |
| (33) | 5-Methoxyethyl-1-methyl-1H,5H-imidazo[4,5-c]quinolin-4-one |
| (34) | 5-Isobutyl-1-methyl-1H,5H-imidazo[4,5-c]quinolin-4-one |
| (35) | 1-Methyl-5-n-pentyl-1H,5H-imidazo[4,5-c]quinolin-4-one |
| (36) | 5-Benzyl-1-methyl-1H,5H-imidazo[4,5-c]quinolin-4-one |

*W in the compound number shows a salt of the compound.

TABLE 2

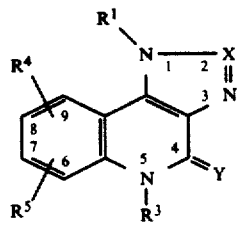

| Compound No. (Example) | R¹ | X | R³ | R⁴/R⁵ | Y |
|---|---|---|---|---|---|
| 1 (1) | CH₃ | CH | (CH₂)₃CH₃ | H | O |
| 2 (2) | CH₃ | CH | CH₂CO₂C(CH₃)₃ | H | O |
| 3 (3) | CH₃ | CH | CH₂-furyl | H | O |
| 4 (4) | CH₃ | CH | CH₃ | H | O |
| 5 (5) | CH₃ | CH | C₂H₅ | H | O |
| 6 (6) | CH₃ | CH | (CH₂)₂CH₃ | H | O |
| 7 (7) | CH₂-phenyl | CH | (CH₂)₃CH₃ | H | O |
| 8 (8) | H | CH | (CH₂)₃CH₃ | H | O |
| 9 (9) | CH₃ | CH | CH₂CO₂H | H | O |
| 10W (10) | CH₃ | C-phenyl | (CH₂)₃CH₃ | H | O |
| 11W (11) | CH₃ | C—CH₃ | (CH₂)₃CH₃ | H | O |
| 12 (12) | CH₃ | CBr | (CH₂)₃CH₃ | 8-Br | O |
| 13 (12) | CH₃ | CH | (CH₂)₃CH₃ | 8-Br | O |

TABLE 2 -continued

[Structure: quinoline-based compound with R¹-N at position 1, X at position 2 (double bond to N at position 3), Y at position 4, R³-N at position 5, R⁴ at position 8/9, R⁵ at position 6/7]

| Compound No. (Example) | R¹ | X | R³ | R⁴/R⁵ | Y |
|---|---|---|---|---|---|
| 14 (13) | CH₃ | CH | (CH₂)₃CH₃ | 8-NO₂ | O |
| 15W (14) | CH₃ | C-(2-furyl) | (CH₂)₃CH₃ | H | O |
| 16W (15) | C₂H₅ | CH | (CH₂)₃CH₃ | H | O |
| 17W (16) | (CH₂)₂CH₃ | CH | (CH₂)₃CH₃ | H | O |
| 18W (17) | CH(CH₃)₂ | CH | (CH₂)₃CH₃ | H | O |
| 19W (18) | (CH₂)₃CH₃ | CH | (CH₂)₃CH₃ | H | O |
| 20W (19) | CH₃ | C-(4-methoxyphenyl) | (CH₂)₃CH₃ | H | O |
| 21W (20) | CH₃ | C-(3,4-dichlorophenyl) | (CH₂)₃CH₃ | H | O |
| 22W (21) | CH₃ | C-cyclopentyl | (CH₂)₃CH₃ | H | O |
| 23W (22) | CH₃ | CH | (CH₂)₃CH₃ | 7-OCH₃, 8-OCH₃ | O |
| 24W (23) | CH₃ | CH | (CH₂)₃CH₃ | 7-Cl | O |
| 25 (24) | CH₃ | CH | (CH₂)₃CH₃ | 8-Cl | O |
| 26 (25) | CH₃ | CH | (CH₂)₃CH₃ | 8-CH₃ | O |
| 27W (26) | CH₃ | CH | (CH₂)₃CH₃ | 9-CH₃ | O |
| 28W (27) | CH₃ | CH | (CH₂)₃CH₃ | H | S |
| 29 (28) | phenyl | CH | (CH₂)₃CH₃ | H | O |
| 30 (29) | CH₃ | C—OH | (CH₂)₃CH₃ | H | O |
| 31 (30) | CH₃ | C—SH | (CH₂)₃CH₃ | H | O |
| 32 (31) | CH₃ | N | (CH₂)₃CH₃ | H | O |
| 33 (32) | CH₃ | CH | (CH₂)₂OCH₃ | H | O |
| 34 (33) | CH₃ | CH | CH₂CH(CH₃)₂ | H | O |
| 35 (34) | CH₃ | CH | (CH₂)₄CH₃ | H | O |
| 36 (35) | CH₃ | CH | —CH₂-phenyl | H | O |

The pharmacological activities of the Compound (I) represented by the general formula (I) are illustrated in (a) a test for effects on passive Schultz-Dale reaction. (b) a test for antiallergic effects, (c) a test for effects on experimental asthma (d) acute toxicity test. The tests are described in detail as follows.

(a) Effects on passive Schultz-Dale reaction (broncho-dilatory effects).

Guinea pigs were passively sensitized as follows. Hartley male guinea pigs weighing 350 to 500 g were injected intraperitoneally with rabbit anti-egg albumin (EWA) serum prepared by the method of Eda et al. [Folia pharmacol., Japon 66, 237, (1970)]. After 24 hours, the guinea pigs were stunned and exsanguinated, and then trachea was excised. The zig-zag strips of the tranchea were prepared by the method of Emmerson and Mackay [J. Pharm. Pharmacol., 31, 798, (1979)]. The strips were suspended in Krebs-Henseleit solution at 37° C. under aeration of a mixed gas of 95% oxygen and 5% carbon dioxide, and incubated for one hour. Antigen (EWA) was then introduced in the solution (final concentration; 1 μg/ml), and the contraction was measured by isotonictrasducer (TD-112s, made by Nihon Kohden K.K., Japan) and recorded on a recorder (Type 3066, made by Yokogawa-Hokushin Denki, K.K. Japan). After the contraction curves reached plateau, the compounds were successively added in order to get cumulative concentration-relaxation curves. Concentration of 50% relaxation rate ($IC_{50}$) was calculated from the regression line, which was obtained from cumulative concentration-relaxation curves.

The results are shown in Table 3.

(b) Antiallergic effects

Antiallergic effects of compounds were assessed by passive cutaneous anaphylaxis (PCA) test in rats. Wistar male rats weighing 180 to 220 g were used for collection of antiserum and Wistar male rats weighing 120 to 140 g for PCA test.

(i) Preparation of anti EWA serum in rat

Anti-EWA rat serum was prepared by the method of Stotland and Share [Can. J. Physiol. Pharmacol., 52, 1114, (1974)] as follows. That is, 1 mg of EWA, 20 mg of aluminium hydroxide gel and 0.5 ml of mixed vaccine of pertussis, diphtheria and tetanus were mixed, and the mixture was subcutaneously injected in 4 portions into the foot part of the rats. After 14 days, the blood of sensitized rats was collected from carotid artery. The serum was separated by centrifugation from collected blood, and kept at −80° C. Titer of the 48 hour homologous PCA tests of the serum was 1:32.

(ii) Effects on 48 hour-homologous PCA tests in rats

Groups each consisting of three male rats were used, and 0.05 ml of anti-EWA serum diluted to 8 times with a physiological saline, was sensitized passively by giving intradermal injection at two depilated points on the dorsum. After 47 hours, the test compound or its solvent (saline or CMC solution) was orally administrated, and 1 hour thereafter, PCA reaction was induced by intravenous administration of 1% Evan's blue-saline (0.5 ml/100 g) containing 2 mg of anti-EWA. After 30 minutes, animals were sacrificed by bleeding and dorsal skin was stripped to determin the extravasated dye at blue-dyed reaction site, by the method of Katayama et al. [Microbiol. Immunol., 22, 89 (1978)]. The blue-dyed spots were scissored out and placed in a test tube containing 1 ml of 1N sodium hydroxide and incubated at 37° C. for 24 hours. 9 ml of a mixture of 0.6N phosphate-:acetone (5:13) was added thereto. After shaking, the mixture was centrifuged at 2500 rpm for 10 minutes. A supernatant was separated, and extravasated dye in the supernatant was quantified by measuring absorbance of the supernatant at 620 nm. Prepared calibration curve was used for the quantification. An average of measurements at the two positions was made a value for one animal, and suppression rate of the one animal was calculated by following equation:

Suppression rate (%) =

$$\frac{\text{Mean of extravasated dye of solvent-administrated group} - \text{Mean of extravasated dye of test compound-administrated group}}{\text{Mean of extravasated dye of solvent-administrated group}} \times 100$$

Cases where, the suppression rate is 50% or higher, were regarded as positive PCA suppression activity, and the minimum administrated dosage, where a positive case was observed in at least one of three animals was regarded as minimum effective dosage (MED).

The results are shown in Table 3.

(c) Effects on experimental asthma

Guinea pigs were passively sensitized as follows. Hartley male guinea pigs weighing 350 to 500 g were intraperitoneally injected with 1 ml of rabbit EWA serum prepared by the method of Eda et al. [Folia pharmacol., Japon, 66, 237 (1970)]. The animals were treated with intraperitoneal injection of diphenhydramine (20 mg/kg) and propranolol (5 mg/kg), 30 minutes before administration of test compounds. 17 hours after the sensitization, the test compounds (50 mg/kg) were orally administrated to sensitized animals. After one hour from the administration of the test compounds, the guinea pigs were placed in plastic observation box and were exposed to an aerosal antigen of 1.5% EWA.

The time until the onset of respiratory distresslike symptom [collapse time (second)] was measured as a result of experimental asthma.

The results are shown in Table 3. The results suggest that the test compounds except Compound 31, have prolonged collapse time from control (saline administrated) and have superior or equivalent effects to that of theophylline.

(d) Acute toxicity

The compounds were orally administrated (po: 300 mg/kg) to male dd-mice weighing 20 to 25 g. $LD_{50}$ was determined by observing the mortality for seven days after the administration.

The results are shown in Table 3.

TABLE 3

| Compound No. | Passive Schultz-Dale reaction ($IC_{50}$; μm) | Anti-allergic effect (MED; mg/kg) | Experimental asthma (Second*4) | Acute Toxicity ($LD_{50}$; mg/kg) |
|---|---|---|---|---|
| 1 | 0.0034 | <10 | 517 ± 37 | >300 |
| 3 | >20 | >100 | | >300 |
| 4 | >20 | >10 | | >200 |
| 5 | >20 | <10 | 519 ± 78 | >100 |
| 6 | <20 | <10 | 600 ± 0 | >200 |
| 7 | >20 | >100 | | >300 |
| 8 | >20 | >100 | | >300 |
| 9 | >20 | >100 | 532 ± 31 | >300 |
| 16W | 4.1 | >100 | 422 ± 43 | >300 |
| 17W | 2.4 | >100 | 484 ± 31 | >300 |
| 18W | 1.5 | >100 | 425 ± 50 | >300 |
| 19W | 6.4 | >100 | 503 ± 44 | >300 |
| 24W | 0.9 | >100 | | >300 |
| 26 | 9.8 | 100 | | >300 |
| 27W | >20 | 100 | | >300 |
| 31 | 9.6 | >100 | 284 ± 48 | >300 |
| 32 | 1.6 | >100 | | >300 |
| Reference Compounds | | | | |
| phylline*1 | 23 | ≦100 | | |
| Enprofylline*2 | 10 | ≦100 | | |
| KC 404*3 | 0.86 | >100 | | |
| Control | | | 254 ± 18 | |
| Theophyl- | | | 414 ± 47 | |

TABLE 3-continued

| Compound No. | Passive Schultz-Dale reaction ($IC_{50}$; μm) | Anti-allergic effect (MED; mg/kg) | Experimental asthma (Second[*4]) | Acute Toxicity ($LD_{50}$; mg/kg) |
|---|---|---|---|---|
| line[*5] | | | | |

[*1] The Merk Index. 11th, pp477, (1989)
[*2] Eur. J. Clin. Pharmacol., 30, 21, (1986)
[*3] Arch. Int. Pharmacodyn., 283, 153 (1986)
[*4] The value represents mean + SEM of 5 or 10 animals
[*5] The Merk Index, 11th, pp1461, (1989)

Compounds (I) or their pharmaceutically acceptable salts are used directly or in various dosage forms. In the present invention, pharmaceutical compositions are prepared by homogeneously mixing an effective amount of Compound (I) or its pharmaceutically acceptable salt with pharmaceutically acceptable carrier. It is desirable that the pharmaceutical compositions are an appropriative dosable unit for oral administration or injection administration.

In the preparation of orally administrated forms, any of useful pharmaceutically acceptable carriers are used. In the case of orally administrated liquid preparates such as suspensions and syrups, for example, water, saccharides such as sucrose, sorbitol, fructose, etc., glycols such as polyethyleneglycol, propyleneglycol, etc., oils such as sesame oil, olive oil, soybean oil, etc., antiseptics such as p-hydroxybenzoic acid esters, etc., and flavors such as strawberry flavor, peppermint etc. are used. In the case of powder, pills, capsules and tablets; vehicles such as lactose, glucose, sucrose, mannitol, etc.; disintegrators such as starch, sodium alginate, etc.; lubricants such as magnesium stearate, talc, etc.; binders such as polyvinyl alcohol, hydroxypropyl cellulose, gelatin, etc., surfactants such as fatty acid esters etc., and plasticizers such as glycerine, etc., are used. Tablets and capsules are most useful dosage form for oral administration because of easy administration. In the preparation of tablets and capsules, solid medicament carriers are used.

Injection solutions are prepared with such a carrier as distilled water, a salt solution, a glucose solution, or a mixture of a salt solution and a glucose solution.

Effective dose and the number of administration of Compound (I) or its pharmaceutically acceptable salt depend on modes of administration and ages, body weight, and symptoms, etc. of patients. It is preferable to usually administate 1 to 50 mg/kg of Compound (I) or its pharmaceutically acceptable salt daily in 3 to 4 portions.

Furthermore, Compound (I) is administered by inhalation in the form of aerosol, finely pulverized powders, or spray solution. In the case of aerosol administration, the present compound are dissolved in an appropriately pharmaceutically acceptable solvent, for example, ethyl alcohol or a combination of miscible solvents and then mixed with a pharmaceutically acceptable propellant. The aerosol composition is used by filling it in a pressure-withstanding container composition. It is preferable that the aerosol value is a metering valve for discharging an effective dosage of aerosol composition as determined in advance.

The present invention will be described in detail below, referring to Examples and Reference Examples.

Yields and physico-chemical properties of the compounds obtained in Examples 1 to 35 are shown in Table 4.

EXAMPLE 1

5-n-Butyl-1-methyl-1H,5H-imidazo[4,5-c]quinolin-4-one (Compound 1)

3.0 g (0.015 mole) of 4-hydroxy-1-methyl-1H-imidazo[4,5-c]quinoline was suspended in 50 ml of dimethylformamide, and 0.80 g (0.020 mole) of 60% sodium hydride was added with ice cooling, followed by stirring at 50° C. for 30 minutes. Then, the mixture was again ice-cooled and 2.6 ml (0.023 mole) of n-butyl iodide was added dropwise, followed by stirring at 50° C. for 2 hours. The solvent was evaporated under reduced pressure, and water was added to the residues, followed by extraction with chloroform. The extract was washed with an aqueous saturated sodium chloride solution, dried over anhydrous sodium sulfate and filtered. The solvent was evaporated under reduced pressure. The residue was purified by silica gel column chromatography (eluting solvent: chloroform/methonal=17/1), followed by recrystallization from isopropanol-isopropyl ether, to afford 2.5 g of Compound 1.

The following Examples 2 to 7 were performed by the method of Example 1.

EXAMPLE 2

5-tert-Butoxycarbonylmethyl-1-methyl-1H,5H-imidazo[4,5-c] quinolin-4-one (Compound 2)

EXAMPLE 3

5-Furfuryl-1-methyl-1H,5H-imidazo[4,5-c]quinolin-4-one (Compound 3)

EXAMPLE 4

1,5-Dimethyl-1H,5H-imidazo[4,5-c]quinolin-4-one (Compound 4)

EXAMPLE 5

5-Ethyl-1-methyl-1H,5H-imidazo[4,5-c]quinolin-4-one (Compound 5)

EXAMPLE 6

1-Methyl-5-n-propyl-1H,5H-imidazo[4,5-c]quinolin-4-one (Compound 6)

EXAMPLE 7

1-Benzyl-5-n-butyl-1H,5H-imidazo[4,5-c]quinolin-4-one (Compound 7)

EXAMPLE 8

5-n-Butyl-1H,5H-imidazo[4,5-c]quinolin-4-one (Compound 8)

2.4 g (0.071 mole) of Compound 7 obtained in Example 7 was dissolved in 115 ml of acetic acid, and 0.48 g of 10% palladium/carbon was added, followed by stirring under a hydrogen gas stream at 70° C. for 4 hours. Then, the reaction solution was filtered and the filtrate was concentrated under reduced pressure. A saturated aqueous sodium hydrogen carbonate was added to neutralize the concentrate, and the precipitated was collected by filtration and recrystallized from ethanol-water, to afford 1.5 g of Compound 8.

EXAMPLE 9

5-Carboxymethyl-1-methyl-1H,5H-imidazo[4,5-c]quinolin-4-one (Compound 9)

2.3 g (0.0074 mole) of Compound 2 obtained in Example 2 was dissolved in 50 ml of methylene chloride, and 50 ml of trifluoroacetic acid was added with ice cooling, followed by stirring at room temperature for 3 hours. Then, the solvent was evaporated under reduced pressure, and diethyl ether was added to the residues, and the thus formed precipitate was collected by filtration, and was recrystallized from dimethylformamide-isopropyl alcohol to afford 1.5 g of Compound 9.

EXAMPLE 10

5-n-Butyl-1-methyl-2-phenyl-1H,5H-imidazo[4,5-c]quinolin-4-one hydrochloride (Compound 10W)

From 0.85 g (3.1 mmols) of Compound c obtained in Reference Example 3 and 0.80 ml (6.2 mmols) of n-butyl iodide, 0.75 g of Compound 10 was obtained in the same manner as in Example 1.

The compound was dissolved in ethyl acetate, and an ethyl acetate saturated by hydrogen chloride was added, and the formed crystals were collected to afford Compound 10W.

EXAMPLE 11

5-n-Butyl-1,2-dimethyl-1H,5H-imidazo[4,5-c]quinolin-4-one hydrochloride (Compound 11W)

From 0.24 g (1.1 mmols) of 4-hydroxy-1,2-dimethyl-1H, 5H-imidazo[4,5-c]quinoline and 0.25 ml (2.2 mmols) of n-butyl iodide, 0.21 g of Compound 11 was obtained in the same manner as in Example 1.

The thus obtained compound was dissolved in ethyl acetate, and an ethyl acetate saturated by hydrogen chloride was added, and the formed precipitate was collected to afford Compound 11W.

EXAMPLE 12

2,8-Dibromo-5-n-butyl-1-methyl-1H,5H-imidazo[4,5-c]quinolin-4-one (Compound 12) and
8-bromo-5-n-butyl-1-methyl-1H,5H-imidazo[4,5-c]quinolin-4-one (Compound 13)

At first, 63 mg (0.78 mmol) of sodium acetate and 0.071 ml (0.39 mmol) of bromine were added to 5 ml of an aqueous chloroform containing 100 mg (0.39 mmol) of Compound 1 obtained in Example 1, followed by stirring at room temperature for 30 minutes. Then, the mixture was neutralized with a saturated aqueous hydrogen carbonate. The organic layer was washed with brine, dried over anhydrous sodium sulfate and filtered. The solvent was evaporated under reduced pressure. The residue was purified by silica gel column chromatography (eluting solvent: chloroform/methanol=20/1), to afford 20 mg of Compound 12 and 20 mg of Compound 13.

EXAMPLE 13

5-n-Butyl-1-methyl-8-nitro-1H,5H-imidazo[4,5-c]quinolin-4-one (Compound 14)

A solution of 100 mg (0.39 mmol) of Compound 1 obtained in Example 1 in 0.13 ml of sulfuric acid was added dropwise to an acid mixture consisting of 0.045 ml of 61% nitric acid and 0.35 ml of 96% sulfuric acid with ice cooling, followed by stirring for 30 minutes. After neutralization with an aqueous 50% sodium hydroxide, the mixture was extracted with chloroform. The organic layer was washed with brine, dried over anhydrous sodium sulfate and filtered. The solvent was evaporated under reduced pressure. The obtained crude product was purified by silica gel column chromatography (eluting solvent: chloroform/methanol=10/1) to afford 13 mg of Compound 14.

EXAMPLE 14

5-n-Butyl-2-furyl-1-methyl-1H,5H-imidazo[4,5-c]quinolin-4-one hydrochloride (Compound 15W)

From 0.31 g (1.2 mmols) of 2-furyl-4-hydroxyl-1-methyl-1H,5H-imidazo[4,5-c]quinoline and 0.27 ml (2.3 mmols) of n-butyl iodide, 0.24 g of Compound 15 was obtained in the same manner as in Example 1.

The obtained compound was dissolved in ethyl acetate and an ethyl acetate saturated by hydrogen chloride was added, and the formed precipitate was collected to afford Compound 15W.

EXAMPLE 15

5-n-Butyl-1-ethyl-1H,5H-imidazo[4,5-c]quinolin-4-one hydrochloride (Compound 16W)

3.3 g (0.011 mole) of Compound e in Reference Example 5 was suspended in 100 ml of ethanol, and 0.70 g of 10% palladium/carbon was added, followed by blowing with hydrogen at room temperature for 4 hours. After removed of the catalyst by filtration, the solvent was evaporated under reduced pressure. Then, 19 ml (0.11 mole) of ethyl orthoformate was added to the obtained residues, followed by stirring at 110° C. for one hour. The ethyl orthoformate was evaporated under reduced pressure, and the residues were dissolved in chloroform. Then, the solution was filtered and 10 ml of ethyl acetate saturated by hydrogen chloride was added. Then the mixture was triturated in ethyl acetate. The precipitate was collected by filtration, washed with ethyl acetate and dried, whereby 3.0 g of Compound 16W was obtained.

EXAMPLE 16

5-n-Butyl-1-n-propyl-1H,5H-imidazo[4,5-c]quinolin-4-one hydrochloride (Compound 17W)

Compound 17W was obtained form Compound f obtained in Reference Example 6 in place of Compound e of Example 15 basically according to the method in Example 15.

EXAMPLE 17

5-n-Butyl-1-isopropyl-1H,5H-imidazo[4,5-c]quinolin-4-one hydrochloride (Compound 18W)

Compound 18W was obtained from Compound g obtained in Reference Example 7 in place of Compound e of Example 15 in basically according to the method in Example 15.

EXAMPLE 18

1,5-Di-n-butyl-1H,5H-imidazo[4,5-c]quinolin-4-one hydrochloride (Compound 19W)

Compound 19W was obtained from Compound h obtained in Reference Example 8 in place of Compound h of Example 15 basically according to the method in Example 15.

EXAMPLE 19

5-n-Butyl-2-(4-methoxyphenyl)-1-methyl-1H,5H-imidazo [4,5-c]quinolin-4-one hydrochloride (Compound 20W)

Compound 20W was obtained from Compound m obatined in Reference Example 13 basically according to the method in Example 10.

EXAMPLE 20

5-n-Butyl-2-(3,4-dichlorophenyl)-1-methyl-1H,5H-imidazo [4,5-c]quinolin-4-one hydrochloride (compound 21W)

An intermediate compound was obtained from Compound i obtained in Reference Example 9 in the same manner as in Reference Examples 2 and 3. Without purifying the intermediate compound, Compound 21W was obtained therefrom in the same manner as in Example 10.

EXAMPLE 21

5-n-Butyl-2-cyclopentyl-1-methyl-1H,5H-imidazo[4,5-c] quinolin-4-one hydrochloride (Compound 22W)

Compound 22W was obtained from Compound o obtained in Reference Example 15 in the same manner as in Example 10.

EXAMPLE 22

5-n-Butyl-7,8-dimethoxy-1-methyl-1H,5H-imidazo[4,5-c] quinolin-4-one hydrochloride (Compound 23W)

Compound 23W was obtained from Compound q obtained in Reference Example 17 in the same manner as in Example 10.

EXAMPLE 23

5-n-Butyl-7-chloro-1-methyl-1H,5H-imidazo[4,5-c]quinolin-4-one hydrochloride (Compound 24)

Compound 24W was obtained from Compound r obtained in Reference Example 18 in the same manner as in Example 10.

EXAMPLE 24

5-n-Butyl-8-chloro-1-methyl-1H,5H-imidazo[4,5-c]quinolin-4-one (Compound 25)

Compound 25 was obtained from compound s obtained in Reference Example 19 in the same manner as in Example 10.

EXAMPLE 25

5-n-Butyl-1,8-dimethyl-1H,5H-imidazo[4,5-c]quinolin-4-one (Compound 26)

Compound 26 was obtained from Compound t obtained in Reference Example 20 in the same manner as in Example 10.

EXAMPLE 26

5-n-Butyl-1,9-dimethyl-1H,5H-imidazo[4,5-c]quinolin-4-one hydrochloride (Compound 27W)

Compound 27W was obtained from Compound u obtained in Reference Example 21 in the same manner as in Example 10.

EXAMPLE 27

5-n-Butyl-1-methyl-1H,5H-imidazo[4,5-c]quinoline-4-thione hydrochloride (Compound 28W)

0.30 g (1.2 mmols) of Compound 1 obtained in Example 1 was suspended in 10 ml of toluene, and 0.48 g (1.2 mmols) of Lawson's reagent was added, followed by refluxing for one hour. The solvent was evaporated under reduced pressure, and the residue was purified by silica gel column chromatography (eluting solvent: chloroform/methanol=50/1) to afford 0.25 g of Compound 28 (78%)

Compound 28 was dissolved in 2 ml of chloroform, and an ethyl acetate saturated with hydrogen chloride gas, was added. The precipitate was collected by filtration to afford Compound 28W.

EXAMPLE 28

1-Phenyl-5-n-butyl-1H,5H-imidazo[4,5-c]quinolin-4-one (Compound 29)

Compound 29 was obtained from Compound v obtained in Reference Example 22 in the same manner as in Example 15.

EXAMPLE 29

5-n-Butyl-2-hydroxy-1-methyl-1H,5H-imidazo [4,5-c]quinolin-4-one (Compound 30)

1.7 g (0.0061 mole) of Compound w obtained in Reference Example 23 was dissolved in 85 ml of ethanol, and 0.34 g of 10% palladium/carbon was added, followed by stirring under hydrogen gas stream at room temperature for 4 hours. After removal of the catalyst by filtration, the solvent was evaporated under reduced pressure, and 30 ml of tetrahydrofuran and 1.5 g (0.0093 mole) of carbonyldiimidazole were added, followed by refluxing with heating for 4 hours. Then, the reaction solution was cooled to room temperature and the precipitate was collected by filtration and washed with isopropyl ether. The obtained precipitate was recrystallized from dimethylformamide-water, to afford 1.2 g of Compound 30.

EXAMPLE 30

5-n-Butyl-1-methyl-2-mercapto-1H,5H-imidazo[4,5-c] quinolin-4-one (Compound 31)

1.7 g (0.0061 mole) of Compound w obtained in Reference Example 23 was dissolved in 85 ml of ethanol, and 0.34 g of 10% palladium/carbon was added, followed by stirring under hydrogen gas stream at room temperature for 4 hours. After removal of the catalyst by filtration, the solvent was evaporated under reduced pressure, and 50 ml of tetrahydrofuran and 1.8 g (0.0092 mole) of thiocarbonyldiimidazole were added, followed by refluxing for 30 minutes. Then, the reaction solution was cooled to room temperature, and the precipitate was collected by filtration and washed with isopropyl ether. The precipitate was recrystallized from ethanol, to afford 1.5 g of Compound 31.

EXAMPLE 31

5-n-Butyl-1-methyl-1H,5H-triazolo[4,5-c]quinolin-4-one (Compound 32)

1.7 g (0.0061 mole) of Compound w obtained in Reference Example 23 was dissolved in 85 ml of ethanol, and 0.34 g of 10% palladium/carbon was added, followed by stirring under hydrogen gas stream at room temperature for 4 hours. After removal of the catalyst by filtration, the solvent was evaporated under reduced pressure. 20 ml of ethanol was added, followed by addition of 0.55 ml of concentrated hydrochloric acid and 15 ml of water with stirring at 0° C. Then, a solution of 0.56 g (0.0080 mole) of sodium nitrate in 6 ml of water was dropped. After 30 minutes, the precipitate was collected by filtration, and was recrystallized from dimethylformamide-water, to afford 1.1 g of Compound 32.

The following Examples 32 to 36 were performed by the method in Example 1.

EXAMPLE 32

5-Methoxyethyl-1-methyl-1H,5H-imidazo[4,5-c]quinolin-4-one (Compound 33)

EXAMPLE 33

5-Isobutyl-1-methyl-1H,5H-imidazo[4,5-c]quinolin-4-one (Compound 34)

EXAMPLE 34

1-Methyl-5-n-pentyl-1H,5H-imidazo[4,5-c]quinolin-4-one (Compound 35)

EXAMPLE 35

5-Benzyl-1-methyl-1H,5H-imidazo[4,5-c]quinolin-4-one (Compound 36)

TABLE 4

| Compound No. | Yield* (%) | Melting Point (°C.) Recrystallization solvent | Elemental analysis (%) upper line: found lower line: calculated | | | IR MS (m/z) | (KBr) cm$^{-1}$ | NMR (Measuring solvent) δ (ppm) |
|---|---|---|---|---|---|---|---|---|
| | | | | C | H | N | | | |
| 1 | 65 | 208~209 | $C_{15}H_{17}N_3O$ | 70.63 | 6.73 | 16.22 | 255 (M+) | 1645, 1004, 791 | (DMSO-d$_6$) 0.94(t,3H,J=7Hz),1.31~1.47(m,2H),1.54~1.68(m,2H), 4.17 (s,3H),4.34(t,2H,J=7Hz),7.34(t,1H, J=9Hz),7.61)t,1H,J=9Hz),7.63(d,1H, J=9Hz),8.10(s,1H),8.20(d,1H,J=9Hz) |
| | | | | 70.56 | 6.71 | 16.46 | | | |
| 2 | 57 | — | — | | | | — | — | (CDCl$_3$) 1.43(s,9H), 4.12(s,3H), 5.12(s,2H),7.05~7.47(m,3H),7.69 (s,1H),7.93(t,1H,J=9Hz) |
| 3 | 50 | >300 dimethylformamide-isopopyl ether | | | | | 279 (M+) | 1635, 786 | (DMSO-d$_6$) 4.17(s,3H), 5.62(s,2H), 6.30~6.37(m2H),7.34(t,1H,J=9Hz), 7.52~7.55(m,2H),7.75(d,1H,J=9Hz), 8.13(s,1H), 8.20(t,1H,J=9Hz) |
| 4 | 46 | 296~298 methanol isopopyl ether | $C_{12}H_{11}N_3O.0.2H_2O$ | 66.38 | 5.09 | 18.96 | 231 (M+) | 1644, 931 | (DMSO-d$_6$) 3.70(s,3H), 4.18(s,3H), 7.37(t,1H,J=9Hz),7.61(t,1H,J=9Hz), 7.64(d,1H,J=9Hz),8.19(brs,1H),8.21 (d,1H,J=9Hz) |
| | | | | 66.46 | 5.29 | 19.27 | | | |
| 5 | 71 | 216~218 isopropanol isopropyl ether | $C_{13}H_{13}N_3O.0.1H_2O$ | 68.32 | 5.71 | 17.90 | 227 (M+) | 1650, 907 | (DMSO-d$_6$) 1.24(t,3H,J=7Hz),4.17(s, 3H),4.38(q,2H,J=7Hz),7.33(t,1H,J=9 Hz)7.58(t,1H,J=9Hz),7.65(d,1H,J=9 Hz),8.11(brs,1H),8.19(d,1H,J=9Hz) |
| | | | | 68.17 | 5.81 | 18.34 | | | |
| 6 | 73 | 231~235 isopropanol isopropyl ether | $C_{14}H_{15}N_3O$ | 69.56 | 6.33 | 17.11 | 241 (M+) | 1652, 886 | (DMSO-d$_6$) 0.96(t,3H,J=7Hz), 1.67~1.74(m,2H),4.17(s,3H),4.31(t,2H,J=7Hz),7.33(t,1H,J=9Hz),7.56(t,1H,J=9Hz),7.65(d,1H,J=9Hz),8.12(brs,1H), 8.17(d,1H,J=9Hz) |
| | | | | 69.69 | 6.27 | 17.41 | | | |
| 7 | 76 | 230~233 ethanol water | $C_{21}H_{21}N_3O$ | 76.31 | 6.43 | 12.42 | 331 (M+) | 1650, 789 | (DMSO-d$_6$) 0.98(t,3H,J=7Hz), 1.40~1.60(m,2H),1.70~1.83(m,2H),4.42 (t,2H,J=7Hz),5.70(s,2H),7.04~7.16 (m,3H),7.28~7.48(m,5H),7.83(s,1H) |
| | | | | 76.11 | 6.39 | 12.68 | | | |
| 8 | 86 | 269~271 ethanol water | $C_{14}H_{15}N_3O$ | 69.86 | 6.30 | 17.29 | 241 (M+) | 3104, 1651, 1520, 1036, 691 | (DMSO-d$_6$)0.95(t,3H,J=7Hz),1.33~1.51(m,2H),1.57~1.73(m,2H),4.36(t, 2H,J=7Hz),7.34(t,1H,J=9Hz),7.55(t, 1H,J=9Hz),7.62(d,1H,J=9Hz),8.23(s, 1H),13.40~13.70(brs,1H) |
| | | | | 69.69 | 6.27 | 17.41 | | | |
| 9 | 77 | 215~218 dimethylformamide isopropylalcohol | — | | | | 257 (M') | 3700~2200, 1651, 823 | (DMSO-d$_6$) 4.19(s,3H),5.12(s,2H), 7.36(t,1H,J=9Hz),7.46(d,1H,J=9Hz), 7.56(t,1H,J=9Hz),8.13(s,1H),8.23(d, 1H,J=9Hz),12.85~13.15(brs,1H) |
| 10W | 74 | 150~155 | $C_{21}H_{21}N_3O.0.5HCl$ | 72.51 | 6.39 | 11.88 | 331 (M+) | 1652 | (DMSO-d$_6$)0.95(t,3H,J=7Hz),1.35~1.49(m,2H), 1.59~1.70(m,2H),4.16 (s,3H),4.39(t,2H,J=7Hz),7.40(t,1H, J=8Hz), 7.61~7.82(m,7H), 8.33(d,1 H,J=8Hz) |
| | | | | 72.14 | 6.20 | 12.02 | | | |
| 11W | 72 | 210~215 | $C_{16}H_{19}N_3O.HCl$ | 62.77 | 6.62 | 13.71 | 269 (M+) | 1672, 1566, 1442, 767 | (DMSO-d$_6$) 0.94(t,3H,J=7Hz),1.37~1.45(m,2H),1.59~1.67(m,2H), 2.78 (s,3H),4.19(s,3H),4.41(t,2H,J=7Hz), 7.49(t,1H,J=7Hz),7.73~7.84(m,2H), 8.40(d,1H,J=8Hz) |
| | | | | 62.84 | 6.59 | 13.74 | | | |
| 12 | 12 | | | | | | 441 (M+) 413 (M++2) 415 (M++4) | | (CDCl$_3$) 0.96(t,3H,J=7Hz), 1.15~1.85(m,4H),4.10(s,3H),4.35(t,2H,J=7Hz),7.31(d,1H,J 9Hz),7.60(dd,1H,J=2, 9Hz),8.07(d,1H,J=2Hz) |
| 13 | 15 | — | — | | | | 333 (M+) 335 (M++2) | — | (CDCl$_3$) 0.98(t,3H,J 7Hz), 1.12~1.86(m,4H),4.13(s,3H),4.36(t,2H,J=7Hz),7.29(d,1H,J=9Hz),7.58(dd,1H, J=2, 9Hz),7.70(s,1H),8.05(d,1H,J=2 |

TABLE 4-continued

| Compound No. | Yield (%) | Melting Point (°C.) Recrystallization solvent | Elemental analysis (%) upper line: found lower line: calculated | IR MS (m/z) | (KBr) cm$^{-1}$ | NMR (Measuring solvent) δ (ppm) |
|---|---|---|---|---|---|---|
| 14 | 11 | — | — | 300 (M+) | — | (CDCl$_3$) 1.01(t,3H,J=7Hz),1.10~2.00(m,4H),4.26(s,3H),4.45(t,2H,J=7Hz),7.56(d,1H,J=9Hz),7.83(s,1H),8.38(dd,1H,J=2.9Hz),8.92(d,1H,J=2 Hz) |
| 15W | 74 | 180~183 | C$_{19}$H$_{19}$N$_3$O$_2$.HCl<br>　　C　　H　　N<br>　63.81　5.61　11.49<br>　63.77　5.63　11.74 | 321 (M+) | 1674 | (DMSO-d$_6$) 0.95(t,3H,J=7Hz),1.38~1.46(m,2H),1.59~1.67(m,2H),4.33 (s,3H),4.38(t,2H,J=7Hz),6.79~6.81 (m,1H),7.27~7.42(m,2H), 7.60~7.71(m,2H),8.04(brs,1H),8.33(d,1H, J=9Hz) |
| 16W | 86 | 190~194 | C$_{16}$H$_{19}$N$_3$O.HCl<br>H$_2$O<br>　　C　　H　　N<br>　59.29　6.55　12.85<br>　59.34　6.84　12.97 | 269 (M+) | 1678 | (DMSO-d$_6$) 0.95(t,3H,J=7Hz),1.51(t, 3H,J=7Hz),4.40(t,3H,J=7Hz),4.76(q, 2H,J=7Hz),8.16(d,1H,J=8Hz), 9.20 (brs,1H) |
| 17W | 81 | 180~183 | C$_{17}$H$_{21}$N$_3$O.HCl<br>　　C　　H　　N<br>　63.74　7.12　13.15<br>　63.84　6.93　13.14 | 283 (M+) | 1672 | (CDCl$_3$) 1.03(t,3H,J=7Hz),1.14(t,3 H,J=7Hz),4.34(t,2H,J=7Hz),5.02(t,2 H,J=7Hz),8.04(d,1H,J=8Hz),10.44(s, 1H),11.09(brs,1H), |
| 18W | 82 | 160~165 | C$_{17}$H$_{21}$N$_3$O.HCl<br>　　C　　H　　N<br>　63.37　7.15　13.02<br>　63.84　6.93　13.14 | 283 (M+) | 1674 | (DMSO-d$_6$) 0.95(t,3H,J=7Hz),1.68(d, 6H,J=7Hz),4.42(t,2H,J=7Hz),8.31(d, 1H,J=8Hz),9.31(s,1H) |
| 19W | 82 | 196~200 | C$_{18}$H$_{23}$N$_3$O.HCl<br>　　C　　H　　N<br>　64.26　7.43　12.42<br>　64.76　7.25　12.57 | 297 (M+) | 1674 | (CDCl$_3$) 4.36(t,2H,J=7Hz),5.04(t,2 H,J=7Hz),8.06(d,1H,J=8Hz),10.38(s, 1H),11.34(brs,1H) |
| 20W | 24 | 157~161 | C$_{22}$H$_{23}$N$_3$O$_2$.HCl<br>　　C　　H　　N<br>　66.37　5.97　10.35<br>　66.41　6.08　10.56 | 361 (M+) | 1669 | (DMSO-d$_6$) 0.96(t,3H,J=7Hz),1.39~1.47(m,2H),1.61~1.70(m,2H),3.89 (s,3H),4.18(s,3H),4.43(t,2H,J=7Hz), 7.22(d,2H,J=9Hz),7.46(t,1H,J=8Hz), 7.68~7.80(m,3H),8.38(d,1H,J=8Hz) |
| 21W | 3 | 174~176 | C$_{21}$H$_{19}$Cl$_2$N$_3$O.<br>HCl<br>　　C　　H　　N<br>　57.53　4.62　9.62<br>　57.75　4.62　9.62 | 399 (M') | 1676 | (DMSO-d$_6$) 0.95(t,3H,J=7Hz),1.37~1.46(m,2H),1.58~1.67(m,2H),4.16 (s,3H),4.38(t,2H,J=7Hz),7.40(t,1H, J=8Hz),7.62~7.90(m,4H),8.07(d,1H, J=2Hz),8.33(d,1H,J=8Hz) |
| 22W | 65 | 153~158 | C$_{20}$H$_{25}$N$_3$O.HCl<br>　　C　　H　　N<br>　66.87　7.61　12.05<br>　66.75　7.28　11.68 | 323 (M+) | 1667 | (DMSO-d$_6$) 0.94(t,3H,J=7Hz),1.36~2.19(m,12H),3.67(quint,1H,J=8Hz), 4.22(s,3H),4.41(t,2H,J=7Hz),7.44(t, 1H,J=7Hz),7.68~7.79(m,2H),8.38(d, 1H,J=8Hz) |
| 23W | 67 | 179~184 | C$_{17}$H$_{21}$N$_3$O$_3$.HCl<br>　　C　　H　　N<br>　57.54　6.00　11.87<br>　58.03　6.30　11.94 | 315 (M+) | 1658 | (DMSO-d$_6$) 0.96(t,3H,J=7Hz),1.37~1.45(m,2H),1.62~1.70(m,2H),3.95 (s,3H,3.97(s,3H),4.33(s,3H),4.43 (t,2H,J=7Hz),7.13(s,1H),7.61(s,1H), 9.10(s,1H) |
| 24W | 63 | 218~222 | C$_{15}$H$_{16}$ClN$_3$O.<br>3/4HCl<br>　　C　　H　　N<br>　56.92　5.41　12.96<br>　56.81　5.32　13.25 | 289 (M+) | 1645 | (DMSO-d$_6$) 0.94(t,3H,J 7Hz),1.36~1.44(m,2H),1.56~1.64(m,2H),4.20 (s,3H),4.37(t,2H,J=7Hz),7.42(brd,1 H,J=9Hz),7.73(brs,1H),8.24(d,1H,J= 9Hz),8.49(s,1H) |
| 25 | 56 | 224~227 | C$_{15}$H$_{16}$ClN$_3$O<br>　　C　　H　　N<br>　62.34　5.61　14.37<br>　62.17　5.57　14.50 | 289 (M+) | 1650 | (DMSO-d$_6$) 0.93(t,3H,J=7Hz(,1.35~1.43(m,2H),1.57~1.63(m,2H),4.17 (s,3H),4.32(t,2H,J=7Hz),7.56~7.67 (m,2H),8.10~8.12(m,2H) |
| 26 | 69 | 186~189 | C$_{16}$H$_{19}$N$_3$O<br>　　C　　H　　N<br>　71.16　7.21　15.80<br>　71.35　7.11　15.60 | 269 (M+) | 1651 | (DMSO-d$_6$) 0.93(t,3H,J=7Hz),1.35~1.43(m,2H),1.57~1.63(m,2H),2.44 (S,3H),4.17(s,3H),4.31(t,2H,J=7Hz) 7.39(brd,1H,J=8Hz),7.41(d,1H,J=8Hz) 7.98(brd,s,1H),8.05(s,1H) |
| 27W | 68 | 160~164 | — | 269 (M+) | 1659 | (DMSO-d$_6$) 0.94(t,3H,J=7Hz),1.34~1.47(m,2H),1.58~1.69(m,2H),2.77 (s,3H),4.09(s,3H),4.36(t,2H,J=7Hz), 7.26(brd,1H,J=6Hz),7.53~7.62(m,2 H),9.00(s,1H) |
| 28W | 78 | 86~88 | C$_{15}$H$_{17}$N$_3$S.HCl<br>　　C　　H　　N<br>　58.53　5.89　13.65<br>　58.75　5.98　13.54 | 271 (M') | 1645, 452 | (CDCl$_3$) 1.02(d,3H,J=7Hz),1.30~2.00(m,4H),4.13(s,3H),4.45~5.50(m 1H),7.20~7.60(m,3H),7.78(s,1H), 8.01(d,2H,J 7Hz) |
| 29 | 50 | 225~227 | C$_{20}$H$_{19}$N$_3$O<br>　　C　　H　　N<br>　75.69　6.03　13.24 | 317 (M+) | 1651, 1517, 775 | (DMSO-d$_6$) 0.96(t,3H,J=7Hz),1.36~1.52(m2H),1.56~1.70(m,2H),4.38 (t,2H,J=7Hz),6.96~7.07(m,2H), |

TABLE 4-continued

| Compound No. | Yield* (%) | Melting Point (°C.) Recrystallization solvent | Elemental analysis (%) upper line: found lower line: calculated | IR MS (m/z) | (KBr) cm$^{-1}$ | NMR (Measuring solvent) δ (ppm) |
|---|---|---|---|---|---|---|
| 30 | 74 | 296~299 dimethylformamide water | 75.50 6.20 13.26<br>$C_{15}H_{17}N_3O_2$<br>C  H  N<br>66.40 6.32 15.49<br>66.56 6.53 15.62 | 271 (M+) | 1712, 1694, 1659 | 7.45~7.77(m,2H),8.28(s,1H)<br>(DMSO-d$_6$) 0.94(t,3H,J=7Hz),1.32~1.46(m,2H),1.54~1.69(m,2H),3.69<br>(s,3H),4.34(t,2H,J=7Hz),7.33(t,1H,J=7Hz),7.56(t,1H,J=7Hz),7.65(d,1H,J 7Hz),8.18(d,1H,J=7Hz) |
| 31 | 85 | 308~317 (ethanol) | 287<br>$C_{15}H_{17}N_3OS$<br>C  H  N<br>62.69 5.96 14.62<br>62.59 6.28 14.28 | 287 (M') | 1663, 1616 | (DMSO-d$_6$) 0.94(t,3H,J=7Hz),1.33~1.49(m,2H),1.60~1.72(m,2H),4.10<br>(s,3H),4.35(t,2H,J=7Hz),7.39(t,1H,J=7Hz(, 7.59~7.70(m,2H),8.29(d,1H,J=7Hz),13.55(brd,s,1H) |
| 32 | 70 | — | — | 256 (M+) | 1670 | (DMSO-d$_6$) 0.95(t,3H,J=9Hz),1.34~1.50(m,2H),1.56~1.72(m,2H),4.35<br>(t,2H,J=7Hz),4.56(s,3H),7.44(t,1H,J=7Hz),7.65~7.76(m,2H),8.28(d,1H,J 7Hz) |
| 33 | 50 | 207~210 isopropanol diisopropyl ether | $C_{14}H_{15}N_3O_2$<br>C  H  N<br>65.36 5.88 16.33<br>65.47 6.09 16.37 | 257 (M+) | 1653, 1246, 1106, 748 | (DMSO-d$_6$) 3.25(s,3H),3.63(t,2H,J=6Hz),4.17(s,3H),4.55(t,2H,J=6Hz),<br>7.33(t,1H,J=7Hz),7.54(t,1H,J=7Hz),7.72(d,1H,J=7Hz),8.09(s,1H),8.19(d,1H,J=7Hz) |
| 34 | 50 | 245~248 | $C_{15}H_{17}N_3O$·HCl<br>C  H  N<br>61.75 6.21 14.40<br>61.28 6.10 14.51 | 255 (M+) | 1675 | (DMSO-d$_6$) 0.92(d,6H,J=7Hz),2.08~2.22(m,1H),4.30(s,3H),4.35~4.80<br>(m,2H),7.44(t,1H,J=7Hz),7.70(t,1H,J=7Hz),7.77(d,1HJ=7Hz),8.30(d,1H,J=7Hz),9.04(brs,1H) |
| 35 | 73 | 234~239 | $C_{16}H_{19}N_2OO$·HCl<br>C  H  N<br>62.84 6.59 13.74<br>62.66 6.60 13.91 | 269 (M+) | 1675 | (DMSO-d$_6$) 0.88(t,3H,J=7Hz),1.25~1.45(m,4H),1.56~1.73(m,2H),4.29<br>(s,3H),4.37(t,2H,J=7Hz),7.45(t,1H,J=7Hz),7.64~7.77(m,2H),8.30(d,1H,J=7Hz),9.04(s,3H) |
| 36 | 48 | 238~243 | $C_{18}H_{15}N_2O$<br>1.0HCl,1.2H$_2$O<br>C  H  N<br>65.62 4.93 12.75<br>65.63 5.01 12.76 | 289 (M+) | 1675 | (DMSO-d$_6$) 4.33(s,3H),5.69(s,2H),<br>7.15~7.48(m,6H),7.55~7.63(m,2H)<br>8.32(d,1H,J=7Hz),9.12(s,1H) |

*Yield was calculated on the basis of free form of the compounds except for Compound Nos. 16W to 19W.

REFERENCE EXAMPLE 1

1-Methyl-2-phenyl-1H-imidazo[4,5-c]quinoline (Compound a)

2.1 g (0.012 mole) of crude product of 3-amino-4-methylaminoquinoline was dissolved in 20 ml of pyridine, and 1.5 ml (0.013 mole) of benzoyl chloride was added followed by stirring at room temperature for one hour. The reaction solution was concentrated under reduced pressure, and 20 ml of phosphorus oxychloride was added to the concentrate, followed by refluxing with heating for 3 hours. The residues obtained by concentration under reduced pressure were dissolved in water and the solution was made alkaline with ammonia water. The precipitate was collected by filtration, washed with water and purified by silica gel column chromatography (eluting solvent: chloroform/methanol=30/1), to afford 2.1 g of Compound a.

NMR(CDCl$_3$) δ (ppm); 4.23 (s,3H), 7.51-7.78 (m, 7H), 8.23-8.33 (m, 2H), 9.35 (s, 1H)

REFERENCE EXAMPLE 2

1-Methyl-2-phenyl-1H-imidazo[4,5-c]quinolin-5-oxide (Compound b)

1.75 g (0.067 mole) of Compound a in Reference Example 1 was dissolved in 26 m( of methylene chloride, and 3.0 g (0.14 mole) of m-chloroperbenzoic acid was added followed by stirring at room temperature for one hour. After reducing excessive peracid by addition of a saturated aqueous sodium sulfite, an aqueous sodium hydrogen carbonate was added and the solution was extracted with methylene chloride. The extract was dried over anhydrous magnesium sulfate, and filtered. The solvent was evaporated under reduced pressure, to afford 1.30 g of crude Compound b.

(NMR (DMSO-d$_6$) δ (ppm); 4.28 (s, 3H), 7.46-7.87 (m, 8H), 8.18 (d, 1H, J=8 Hz), 9.10 (s, 1H)

REFERENCE EXAMPLE 3

4-Hydroxy-1-methyl-2-phenyl-1H-imidazo[4,5-c]quinoline (Compound c)

20 ml of acetic anhydride was added to 1.0 g of Compound b obtained in Reference Example 2, followed by refluxing for 5 hours. After the reaction solution was concentrated under reduced pressure, methanol was added to the residues. The solution was adjusted to a pH of 9 to 10 with sodium methoxide. The precipitate was collected by filtration and washed with methanol, to afford 0.63 g of Compound c.

NMR (DMSO-d$_6$) δ (ppm); 4.15 (s, 3H), 7.46-7.73 (m, 8H), 8.21 (d, 1H, J=8 Hz), 11.5 (s, 1H)

REFERENCE EXAMPLE 4

1-n-Butyl-4-chloro-3-nitro-2(1H)-quinolone (Compound d)

To 2.4 ml (0.026 mole) of ethyl nitroacetate and 30 ml of N,N'-dimethylacetamide (DMA), 1.0 g (0.026 mole) of 60% sodium hydride was added with ice cooling, followed by stirring for 30 minutes. 5.2 g (0.024 mole) of 1-butyl-2H-3,1-benzoxazine-2,4(1H)-dione [J. Heterocycl. Chem., 12, 565 (1975)] in 20 ml of DMA was added, followed by heating to 120° C. After stirring for 5 hours, the solvent was evaporated under reduced pressure, and 15 ml of water and 15 ml of methylene chloride were added to the residues. The precipitate was collected by filtration. The aqueous layer of the filtrate was made acidic with concentrated hydrochloric acid, and the precipitate was recollected by filtration and dried together with the previously recovered crystals.

Then, 16 ml (0.17 mole) of phosphorus oxychloride was added to the dried precipitate, followed by heating at 100° C. for one hour. The solvent was evaporated under reduced pressure, and 10 ml of ice water was added to the residues and neutralized with a 2N sodium hydroxide solution with ice cooling. Then, the mixture was extracted with chloroform. The organic layer was washed with a saturated aqueous sodium chloride, dried over anhydrous sodium sulfate and filtered. The solvent was evaporated under reduced pressure. Then the residue was purified by silica gel column chromatography (eluting solvent: chloroform) to afford 1.1 g of Compound d (16%).

MS (m/z); 280 (M+), 282 (M++2)

NMR (CDCl$_3$) δ (ppm); 1.01 (t, 3H, J=7 Hz), 1.28-1.97 (m, 4H), 4.34 (t, 2H, J=7 Hz), 7.28-7.52 (m, 2H), 7.75 (t, 1H, J=8 Hz), 8.11 (d, 1H, J=8 Hz)

REFERENCE EXAMPLE 5

1-n-Butyl-4-ethylamino-3-nitro-2(1H)-quinolone (Compound e)

3.5 g (0.013 mole) of Compound d in Reference Example 4 was dissolved in 30 ml of tetrahydrofuran, and 8.0 ml (0.13 mole) of ethylamine was added with ice cooling, followed by stirring at room temperature overnight. The solvent was evaporated under reduced pressure and ice water was added to the residue. The precipitate was collected by filtration and dried, to afford 3.5 g of Compound e (97%).

NMR (CDCl$_3$) δ (ppm); 0.98 (t, 3H, J=7 Hz), 1.37 (t, 3H, J=7 Hz), 1.26-2.00 (m, 4H), 3.30-3.68 (m, 2H), 4.24 (t, 2H, J=7 Hz), 6.15-6.42 (m, 1H), 7.10-7.85 (m, 4H)

REFERENCE EXAMPLE 6

1-n-Butyl-3-nitro-4-n-propyl-2(1H)-quinolone (Compound f)

Compound f was obtained from n-propylamine in place of ethylamine of Reference Example 5 basically according to the method in Reference Example 5 (yield: 95%).

NMR(CDCl$_3$) δ (ppm); 0.80-1.20 (m, 6H), 1.22-1.98 (m, 6H), 3.20-3.60 (m, 2H), 4.30 (t, 2H, J=7 Hz), 6.50-6.82 (m, 1H), 7.12-7.86 (m 4H)

REFERENCE EXAMPLE 7

1-n-Butyl-3-nitro-4-isopropyl-2(1H)-quinolone (Compound g)

Compound g was obtained from isopropylamine in place of ethylamine of Reference Example 5 basically according to the method in Reference Example 5 (yield: 90%)

NMR (CDCl$_3$) δ (ppm); 0.99 (t,3H, J=7 Hz), 1.31 (d, 6H, J=6 Hz), 1.15-1.92 (m, 4H), 3.61-4.35 (m, 3H), 5.97-6.35 (m, 1H), 7.03-7.88 (m, 4H)

REFERENCE EXAMPLE 8

1-n-Butyl-4-n-butylamino-3-nitro-2(1H)-quinolone (Compound h)

Compound h was obtained from n-butylamine in place of ethylamine of Reference Example 5 basically according to the method in Reference Example 5 (yield: 96%).

NMR (CDCl$_3$) δ (ppm); 0.78-1.10 (m, 6H), 1.12-1.92 (m, 8H), 3.30-3.61 (m, 2H), 4.23 (t, 2H, J=7 Hz), 6.40-6.72 (m, 1H), 7.02-7.35 (m, 4H), 7.45-7.82 (m, 2H)

REFERENCE EXAMPLE 9

2-(4-Methoxyphenyl)-1-methyl-1H-imidazo[4,5-c]quinoline (Compound i)

Compound i was obtained from 4-methoxybenzoyl chloride in place of benzoyl chloride of Reference Example 1 basically according to the method in Reference Example 1 (yield: 72%)

NMR (CDCl$_3$) δ (ppm); 4.28 (s,3H), 7.04-7.13 (m, 2H), 7.61-7.77 (m, 4H), 8.21-8.40 (m, 2H), 9.35 (s, 1H)

REFERENCE EXAMPLE 10

2-(3,4-Dichlorophenyl)-1-methyl-1H-imidazo[4,5-c]quinoline (Compound j)

Compound j was obtained from 3,4-dichlorobenzoyl chloride in place of benzoyl chloride of Reference Example 1 basically according to the method in Reference Example 1 (yield: 59%).

NMR (CDCl$_3$) δ (ppm); 4.20 (s, 3H), 7.57-7.65 (m, 4H), 7.86-7.89 (m, 1H), 8.19-8.29 (m, 2H), 9.28 (s, 1H)

REFERENCE EXAMPLE 11

2-(2-Furyl)-1-methyl-1H-imidazo[4,5-c]quinoline (Compound k)

Compound k was obtained from 2-furoyl chloride in place of benzoyl chloride of Reference Example 1 basically according to the method in Reference Example 1 (yield: 73%)

NMR (CDCl$_3$) δ (ppm); 4.47 (s, 3H), 6.62-6.68 (m, 1H), 7.18-7.22 (m, 1H), 7.60-7.71 (m, 3H) 8.25-8.45 (m, 2H), 9.32 (s, 1H)

REFERENCE EXAMPLE 12

2-Cyclopentyl-1-methyl-1H-imidazo[4,5-c]quinoline (Compound l)

Compound l was obtained from cyclopentanoyl chloride in place of benzoyl chloride of Reference Example 1 basically according to the method in Reference Example 1 (yield: 62%).

NMR (CDCl$_3$) δ (ppm); 1.65-2.15 (m, 8H), 3.10-3.35 (m, 1H), 4.13 (s, 3H), 7.53-7.70 (m, 2H) 8.21-8.32 (2H, s), 9.23 (s, 3H)

REFERENCE EXAMPLE 13

4-Hydroxy-2-(4-methoxyphenyl)-1-methyl-1H-imidazo[4,5-c] quinoline (Compound m)

Compound m was obtained from Compound i in Reference Example 9 in the same manner as in Reference Examples 2 and 3 (yield: 54%).

NMR (DMSO-d$_8$) δ (ppm); 3.86 (s, 3H), 4.13 (s, 3H), 7.13- 7.75 (m, 7H), 8.21 (d, 1H, J=8 Hz), 11.58 (s, 1H)

REFERENCE EXAMPLE 14

2-(2-Furyl)-4-hydroxy-1-methyl-1H-imidazo[4,5-c]quinoline (Compound n)

Compound n was obtained from compound k in Reference Example 11 in the same manner as in Reference Examples 2 and 3 (yield: 41%).

NMR (DMSO-$d_6$) δ (ppm); 4.31 (s, 3H), 6.76–6.78 (m, 1H), 7.17–7.49 (m, 4H), 7.99 (brs, 1H) 8.23 (d, 1H, J=8 Hz), 11.63 (s, 1H)

REFERENCE EXAMPLE 15

2-Cyclopentyl-4-hydroxy-1-methyl-1H-imidazo[4,5-c]quinoline (Compound o)

Compound o was obtained from Compound l in Reference Example 12 in the same manner as in Reference Examples 2 and 3 (yield: 39%)

NMR (DMSO-$d_6$) δ (ppm); 1.62–2.11 (m, 8H), 3.38–3.47 (m, 1H), 4.08 (s, 1H), 7.20–7.50 (m, 3H), 8.18 (d, 1H, J=8 Hz), 11.48 (s, 1H)

REFERENCE EXAMPLE 16

1,2-Dimethyl-4-hydroxy-1H-imidazo[4,5-c]quinoline (Compound p)

Compound p was obtained from 1,2-dimethyl-1H-imidazo[4,5-c]quinoline as described in Japanese Published Unexamined Patent Application No. 123488/85, [U.S. Pat. Nos. 4698348 and 4689338, and EP-A-145340], in the same manner as in Reference Examples 2 and 3 (yield: 52%)

NMR (DMSO-$d_6$) δ (ppm); 2.52 (s, 3H), 4.04 (s, 3H), 7.22–7.45 (m, 3H), 8.14 (d, 1H, J=8 Hz), 11.46 (s, 1H)

REFERENCE EXAMPLE 17

7,8-Dimethoxy-4-hydroxy-1-methyl-1H-imidazo[4 5-c]quinoline (Compound q)

Compound q was obtained from 7,8-dimethoxy-1-methyl-1H-imidazo[4,5-c]quinoline as described in Japanese Published Unexamined Patent Application No. 123488/85 [U.S. Pat. Nos. 4698348 and 4689338, and EP-A-145340] in the same manner as in Reference Examples 2 and 3 (yield; 51%)

NMR (DMSO-$d_6$) δ (ppm); 3.82 (s, 3H), 3.88 (s, 3H), 4.17 (s, 3H), 7.05 (s, 1H), 7.49 (s, 1H), 7.98 (s, 1H), 11.26 (s, 1H)

REFERENCE EXAMPLE 18

7-Chloro-4-hydroxy-1-methyl-1H-imidazo[4,5-c]quinoline (Compound r)

Compound r was obtained from 7-chloro-1-methyl-1H-imidazo[4,5-c]quinoline as described in Japanese Published Unexamined Patent Application No. 123488/85 [U.S. Pat. Nos. 4698348 and 4689338, and EP-A-145340] in the same manner as in Reference Examples 2 and 3 (yield: 48%).

NMR (DMSO-$d_6$) δ (ppm); 4.15 (s, 3H), 7.28 (brd, 1H, 7 Hz), 7.50 (brs, 1H), 8.10–8.14 (m, 2H) 11.59 (s, 1H)

REFERENCE EXAMPLE 19

8-Chloro-4-hydroxy-1-methyl-1H-imidazo[4,5-c]quinoline (Compound s)

Compound s was obtained from 8-chloro-1-methyl-1H-imidazo[4,5-c]quinoline as described in Japanese Published Unexamined Patent Application No. 123488/85 [U.S. Pat. Nos. 4698348 and 4689338, and EP-A-145340] in the same manner as in Reference Examples 2 and 3 (yield: 26%).

NMR (DMSO-$d_6$) δ (ppm); 4.17 (s, 3H), 7.44–7.52 (m, 2H), 8.05 (brs, 1H), 8.11 (s, 1H), 11.63 (s, 1H)

REFERENCE EXAMPLE 20

1,8-Dimethyl-4-hydroxy-1H-imidazo[4 5-c]quinoline (Compound t)

Compound t was obtained from 1,8-dimethyl-1H-imidazo[4,5-c]quinoline as described in Japanese Published Unexamined Patent Application No. 123488/85 [U.S. Pat. Nos. 4698348 and 4689338, and EP-A-145340] in the same manner as in Reference Examples 2 and 3 (yield: 40%).

NMR (DMSO-$d_6$) δ (ppm); 2.42 (s, 3H), 4.16 (s, 3H) 7.29–7.37 (m, 2H), 7.90 (s, 1H), 8.04 (brs, 1H) 11.38 (s, 1H)

REFERENCE EXAMPLE 21

1,9-Dimethyl-4-hydroxy-1H-imidazo[4,5-c]quinoline (Compound u)

Compound u was obtained from 1,9-dimethyl-1H-imidazo[4,5-c]quinoline as described in Japanese Published Unexamied Patent Application No. 123488/85 [U.S. Pat. Nos. 4698348 and 4689338, and EP-A-145340] in the same manner as in Reference Examples 2 and 3 (yield: 40%)

NMR (DMSO-$d_6$) δ (ppm); 2.76 (s, 3H), 4.04 (s, 3H), 7.07 (brd, 1H, J=7 Hz), 7.28–7.36 (m, 2H), 8.10 (brs, 1H), 11.44 (s, 1H)

REFERENCE EXAMPLE 22

4-Anilino-1-n-butyl-3-nitro-2(1H)-quinolone (Compound v)

Compound v was obtained from aniline in place of ethylamine of Reference Example 5 in substantially the same manner as in Reference Example 5 (yield: 75%).

NMR (CDCl$_3$) δ (ppm); 1.01 (t, 3H, J=6 Hz), 1.22–1.98 (m, 4H), 4.30 (t, 2H, J=7 Hz), 6.80–7.70 (m, 9H), 8.63 (brs, 1H)

REFERENCE EXAMPLE 23

1-n-Butyl-4-methylamino-3-nitro-2-(1H)quinolone (Compound w)

11 g (0.039 mole) of Compound d obtained in Reference Example 4 was dissolved in 100 ml of tetrahydrofuran, and 30 ml (0.39 mole) of 40% methylamine was added with ice cooling, followed by stirring at room temperature for one hour. Then, the solvent was evaporated under reduced pressure, and water was added to the residues. The precipitate was collected by filtration and dried, to afford 9.2 g of Compound w (yield: 87%).

Melting point; 225°–227° C. (isopropanol-diisopropyl ether)

MS(m/z); 275 (M$^+$)

NMR (CDCl$_3$) δ (ppm); 0.95 (t, 3H, J=6 Hz), 1.19–1.89 (m, 4H) 3.10 (d, 3H, J=5 Hz), 4.22 (t, 2H, J=7 Hz) 6.72–7.04 (m, 1H), 7.06–7.40 (m, 2H), 7.58 (t, 1H, J=8 Hz), 7.94 (d, 1H, J=8 Hz)

Pharmaceutical Preparation 1 Tablet
A tablet having the following composition is prepared in a conventional manner.

| | |
|---|---|
| Compound 1 | 50 mg |
| Lactose | 113 mg |
| Potato starch | 30 mg |

-continued

| | |
|---|---|
| Hydroxypropylcellulose | 6 mg |
| Magnesium stearate | 0.6 mg |

Pharmaceutical Preparation 2 Powder
Powders having the following composition are prepared in a conventional manner.

| | |
|---|---|
| Compound 1 | 50 mg |
| Lactose | 750 mg |

Pharmaceutical Preparation 3 Syrup
Syrup having the following composition is prepared in a conventional manner.

| | |
|---|---|
| Compound 1 | 50 mg |
| Refined sugar | 75 mg |
| Ethyl p-hydroxybenzoate | 100 mg |
| Propyl p-hydroxybenzoate | 25 mg |
| Strawberry flavor | 0.25 cc |
| Water is added to make the whole volume 100 cc. | |

Pharmaceutical Preparation 4 Capsule
Capsule having the following composition is prepared in a conventional manner.

| | |
|---|---|
| Compound 1 | 50 mg |
| Avicel | 69.5 mg |
| Magnesium stearate | 0.5 mg |

The composition was mixed and packed in a gelatin capsule.

Pharmaceutical Preparation 5 Injection
Injection having the following composition is prepared in a conventional manner.

| | |
|---|---|
| Compound 1 | 10 mg |
| Buffer agent | proper quantity |

Water for injection was added to the composition to make the whole volume 1.0 ml (amount per 1 ampoule). The solution was distilled and sterilized in an autoclave.

What is claimed is:

1. An imidazoquinolone derivative represented by the formula:

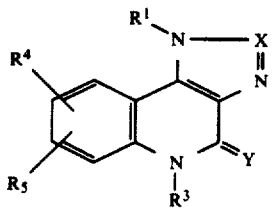

wherein $R^1$ represents hydrogen, alkyl having 1 to 10 carbon atoms, cycloalkyl having 3 to 8 carbon atoms, alkenyl having 2 to 6 carbon atoms, aralkyl having 7 to 15 carbon atoms, aralkenyl having 8 to 18 carbon atoms or aryl having 6 to 10 carbon atoms which is optionally substituted with 1 or 2 substituents independently selected from the group consisting of alkyl having 1 to 6 carbon atoms, trifluoromethyl, hydroxyl, alkoxyl having 1 to 6 atoms, alkylthio having 1 tp 6 carbon atoms, nitro, halogen, amino, alkylamino having 1 to 6 carbon atoms, alkanoylamino having 1 to 6 carbon atoms, alkoxycarbonyl having 2 to 7 carbon atoms, alkanoyl having 1 to 6 carbon atoms and aroyl selected from the group consisting of benzoyl, toluyl, propylbenzoyl and naphtoyl; x represents nitrogen or

where $R^2$ is hydrogen, hydroxyl, alkyl having 1 to 10 carbon atoms, cycloalkyl having 3 to 8 carbon atoms, alkenyl having 2 to 6 carbon atoms, aralkyl having 7 to 15 carbon atoms, aralkenyl having 8 to 18 carbon atoms, aryl having 6 to 10 carbon atoms which is optionally substituted with 1 to 2 substituents independently selected from the same groups as previously defined as to the substituents for aryl, thiol, halogen, aromatic heterocyclic group including heterocyclic rings of 5 or 6 members selected from the group consisting of thienyl, furyl, pyrazolyl, oxazolyl, imidazolyl and pyridyl which are optionally substituted with 1 or 2 substituents independently selected from the group consisting of alkyl having 1 to 6 carbon atoms, alkoxyl having 1 to 6 carbon atoms and halogen, or —(CH$_2$)$_m$CO$_2$R$^6$ where $R^6$ is hydrogen or alkyl having 1 to 6 carbon atoms and m is an integer of 0 to 3; Y represents oxygen or sulfur; $RR^3$ represents alkyl having 1 to 10 carbon atoms, cycloalkyl having 3 to 8 carbon atoms, aklenyl having 2 to 6 carbon atoms, alkoxyalkyl where alkyl moiety has 1 to 10 carbon atoms, aralkyl having 7 to 15 carbon atoms, aralkenyl having 8 to 18 carbon atoms, —(CH$_2$)$_n$—Het where Het has the same meaning as defined as to the aromatic heterocyclic group, and n is an integer of 1 to 3 or —(CH$_2$)$_n$CO$_2$R$^{6a}$ where n has the same meaning as defined above and $R^{6a}$ has the same meaning as defined as to $R^6$; each of $R^4$ and $R^5$ independently represents hydrogen, alkyl having 1 to 6 carbon atoms, trifluoromethyl, cycloalkyl having 3 to 8 carbon atoms, halogen, hydroxyl, alkoxyl having 1 to 6 carbon atoms, alkylthio having 1 to 6 carbon atoms, nitro, amino, alkylamino having 1 to 6 carbon atoms, alkanoyl having 1 to 6 carbon atoms, alkanoylamino having 1 to 6 carbon atoms, aroyl selected from the group consisting of benzoyl, toluyl, propylbenzoyl and naphtoyl or aroylamino where the aroyl moiety has the same meaning as defined as to the aroyl; or a pharmaceutically acceptable salt thereof.

2. A compound according to claim 1, wherein X is

3. A compound according to claim 2, wherein $R^1$ is hydrogen, CH$_3$, C$_2$H$_5$, (CH$_2$)$_2$CH$_3$,

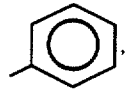

CH(CH$_3$)$_2$, (CH$_2$)$_3$CH$_3$, or

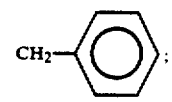

$R^2$ is hydrogen, CH$_3$, hydroxyl, thiol, Br,

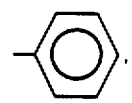

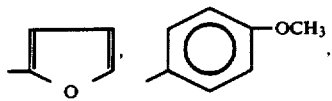 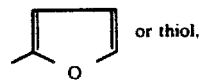

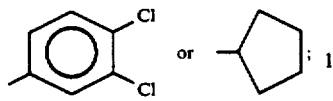

$R^3$ is $CH_3$, $C_2H_5$, $(CH_2)_3CH_3$, $CH_2CO_2C(CH_3)_3$,

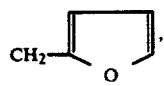

$CH_2CO_2H$, $(CH_2)_2OCH_3$, $CH_2CH(CH_3)_2$, $(CH_2)_4CH_3$ or

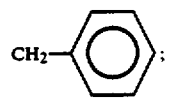

each of $R^4$ and $R^5$ independently represents hydrogen, $CH_3$, $OCH_3$, Cl, Br or nitro.

4. A compound according to claim 3, wherein $R^1$ is hydrogen, $CH_3$,

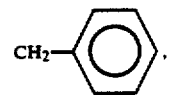

$C_2H_5$, $(CH_2)_2CH_3$, $CH(CH_3)_2$ or $(CH_2)_3CH_3$; $R^2$ is hydrogen,

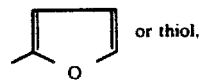 or thiol, $R^3$ is $(CH_2)_3CH_3$, $(CH_2)_2CH_3$,

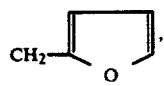

$CH_3$, $C_2H_5$ or $CH_2CO_2H$; each of $R^4$ and $R^5$ independently represents hydrogen $CH_3$ or Cl.

5. A compound according to claim 9 wherein x is nitrogen, $R^1$ is alkyl having 1 to 10 carbon atoms, $R^3$ is alkyl having 1 to 10 carbon atoms, each of $R^4$ and $R^5$ independently represents hydrogen, and Y is oxygen.

6. A compound according to claim 1, which is selected from the group consisting of 5-n-butyl-1-methyl-1H, 5H-imidazo[4,5-c]quinolin-4-one, 1,5-di-n-butyl-1H, 5H-imidazo[4,5-c]quinolin-4-one, 5-n-butyl-1-ethyl-1H, 5H-imidazo[4,5-c]quinolin-4-one, 5-n-butyl-1-propyl-1H, 5H-imidazo[4,5-c]quinolin-4-one, 5-n-butyl-1-isopropyl-1H, 5H-imidazo[4,5-c]quinolin-4-one, 5-n-butyl-7-chloro-1-methyl-1H, 5H-imidazo[4,5-c]quinolin-4-one, 5-n-butyl-1,8-dimethyl-1H, 5H-imidazo[4,5-c]quinolin-4-one, 5-n-butyl-1-methyl-2-mercapto-1H, 5H-triazolo[4,5-c]quinolin-4-one.

7. A compound according to claim 1, wherein said salt is selected from the group consisting of acid addition salt, metal salt, ammonium salt, organic amine addition salt and amino acid addition salt.

8. A pharmaceutical composition comprising a pharmaceutical carrier and as an active ingredient, an effective amount of the compound as defined by claim 1.

* * * * *

UNITED STATES PATENT AND TRADEMARK OFFICE
CERTIFICATE OF CORRECTION

PATENT NO. : 4,994,468

DATED : February 19, 1991

INVENTOR(S) : FUMIO SUZUKI, ET AL.

It is certified that error appears in the above-identified patent and that said Letters Patent is hereby corrected as shown below:

ON THE TITLE PAGE:
IN [56] REFERENCES CITED

Insert:    -- FOREIGN PATENT DOCUMENTS 0145340   5/1985   European Pat. Off.

OTHER PUBLICATIONS

Chem. Abs. Vol. 109, no. 3, 7/18/88, abs. no. 16 630k
    Chem. Abs. Vol. 105, no. 13, 9/29/86, abs. no. 115 064c
    Chem. Abs. Vol. 68, no. 25, 6/17/68, abs. no. 114 396t --.

IN [57] ABSTRACT

Line 4, "kenyl aralkyl," should read --kenyl, aralkyl,--.
    Line 12, "alkoxyalkly," should read --alkoxyalkyl,--.

COLUMN 1

Line 68, "above $R^{6a}$" should read --above and $R^{6a}$--.

COLUMN 5

Line 27, "step 4" should read --Step 4--.
    Line 49, "benzen" should read --benzene--.

COLUMN 8

Line 30, Insert before Table 2 --The formula of these compounds 1 to 36 are shown in Table 2.--.

UNITED STATES PATENT AND TRADEMARK OFFICE
CERTIFICATE OF CORRECTION

PATENT NO. : 4,994,468

DATED : February 19, 1991

INVENTOR(S) : FUMIO SUZUKI, ET AL.

It is certified that error appears in the above-identified patent and that said Letters Patent is hereby corrected as shown below:

COLUMN 9

Line 65, "reaction." should read --reaction,--.
Line 67, "asthma (d)" should read --asthma, and (d)--.

COLUMN 11

Line 3, "tranchea" should read --trachea--.
Line 10, "isotonictrasducer" should read --isotonictransducer--.
Line 51, "determin" should read --determine--.

COLUMN 12

TABLE 3, "phylline*1" should read --amino-phylline*1--
and "0.86 > 100" should read --0.86 phylline*1 > 100--.

COLUMN 13

TABLE 3-continued, "Merk Index" should read --Merck Index-- (both occurrences) and "+ SEM" should read --± SEM--.
Line 20, "appropriative" should read --appropriate--.
Line 49, "administate" should read --administrate--.
Line 61, "value" should read --valve--.
Line 67, "Examples 1 to 35" should read --Examples 1 to 36--.

COLUMN 14

Line 59, "precipitated" should read --precipitate--.

UNITED STATES PATENT AND TRADEMARK OFFICE
CERTIFICATE OF CORRECTION

PATENT NO. : 4,994,468

DATED : February 19, 1991

INVENTOR(S) : FUMIO SUZUKI, ET AL.

It is certified that error appears in the above-identified patent and that said Letters Patent is hereby corrected as shown below:

COLUMN 16

Line 23, "removed" should read --removal--.
Line 40, "form" should read --from--.
Line 58, "h" should read --e--.
Line 67, "obatined" should read --obtained--.

COLUMN 20

TABLE 4, " IR       should     -- MS       IR
     MS   (KBr)    read              (KBr)
    (m/z)  cm⁻¹ "                (m/z)   cm⁻¹ --.

COLUMN 22

TABLE 4-continued,

" IR         should     -- MS       IR
    MS   (KBr)   read              (KBr)
   (m/z) cm⁻¹ "                (m/z)   cm⁻¹ --.

TABLE 4-continued,
    Under Compound No. 23W,
    "(s,3H,3.97" should read --(s,3H), 3.97--.
Under Compound No. 24W,
   "0.94(t,3H,J 7Hz)" should read --0.94(t,3H,J=7Hz)--.
Under Compound No. 25, "0.93(t,3H,J=7Hz(,1.35-"
   should read --0.93(t,3H,J=7Hz), 1.35---.

UNITED STATES PATENT AND TRADEMARK OFFICE
CERTIFICATE OF CORRECTION

PATENT NO. : 4,994,468
DATED : February 19, 1991
INVENTOR(S) : FUMIO SUZUKI, ET AL.

It is certified that error appears in the above-identified patent and that said Letters Patent is hereby corrected as shown below:

COLUMN 23

TABLE 4-continued,

" IR          should     -- MS      IR
MS  (KBr)     read              (KBr)
(m/z) $cm^{-1}$ "                (m/z)  $cm^{-1}$ --.

TABLE 4-continued,
  Under Compound No. 30,
  "J 7Hz)" should read --J=7Hz)--.
  Under Compound No. 31,
  "J=7Hz(," should read --J=7Hz),--.
  Under Compound No. 32,
  "J 7Hz)" should read --J=7Hz)--.

Line 54, "chloform/me-" should read --chloroform/me- --.
Line 63, "26 m(" should read --26 ml--.

COLUMN 24

Line 42, "(NMR" should read --NMR--.

COLUMN 28

Line 25, "Unexamied" should read --Unexamined--.

UNITED STATES PATENT AND TRADEMARK OFFICE
CERTIFICATE OF CORRECTION

PATENT NO. : 4,994,468

DATED : February 19, 1991

INVENTOR(S) : FUMIO SUZUKI, ET AL.

It is certified that error appears in the above-identified patent and that said Letters Patent is hereby corrected as shown below:

COLUMN 29

Line 52, "tp" should read --to--.
    Line 58, "naphtoyl;" should read --naphthoyl;--.

COLUMN 30

Line 14, "RR$^3$" should read --R$^3$--.
    Line 34, "naphtoyl" should read --naphthoyl--.

COLUMN 32

Line 16, "hydrogen CH$_3$" should read --hydrogen, CH$_3$--.
    Line 17, "claim 9" should read --claim 1,-- and "x" should read --X--.
    Line 25, "5-n-butyl-1-pro-" should read --5-n-butyl-1-n-pro- --.

Signed and Sealed this

Twenty-seventh Day of October, 1992

Attest:

DOUGLAS B. COMER

Attesting Officer      Acting Commissioner of Patents and Trademarks